US006492330B1

(12) United States Patent
Mukherjee et al.

(10) Patent No.: US 6,492,330 B1
(45) Date of Patent: Dec. 10, 2002

(54) ANTIANGIOGENIC DRUGS

(75) Inventors: Rama Mukherjee, New Delhi; Manu Jaggi, Ghaziabad; Sudhanand Prasad, Ghaziabad; Anand C. Burman, Ghaziabad; Praveen Rajendran, Ghaziabad; Archana Mathur, Ghaziabad; Anu T. Singh, Ghaziabad, all of (IN)

(73) Assignees: National Institute of Immunology, New Delhi (IN); Dabur Research Foundation, Ghaziabad (IN)

( * ) Notice: Subject to any disclaimer, the term of this patent is extended or adjusted under 35 U.S.C. 154(b) by 0 days.

(21) Appl. No.: 09/248,381

(22) Filed: Feb. 11, 1999

Related U.S. Application Data

(63) Continuation-in-part of application No. 08/727,679, filed on Oct. 8, 1996, now Pat. No. 6,156,725.
(60) Provisional application No. 60/080,433, filed on Apr. 2, 1998.

(30) Foreign Application Priority Data

Aug. 16, 1996 (IN) ........................................ 1822/DEL/96
Feb. 11, 1998 (IN) ........................................ 342/DEL/98

(51) Int. Cl.[7] .............................................. A61K 38/00

(52) U.S. Cl. .............................. 514/12; 514/14; 514/16; 530/309; 530/311; 530/324; 530/327; 530/328

(58) Field of Search .............................. 514/12, 14, 16; 530/311, 309, 324, 327, 328, 329

(56) References Cited

U.S. PATENT DOCUMENTS

| | | | | |
|---|---|---|---|---|
| 5,217,955 A | * | 6/1993 | Bogden et al. | 514/12 |
| 5,273,963 A | | 12/1993 | Moody | 514/12 |
| 5,410,019 A | * | 4/1995 | Coy et al. | 530/323 |
| 5,434,132 A | | 7/1995 | Rozengurt | 514/2 |
| 5,552,520 A | * | 9/1996 | Kim et al. | 530/311 |
| 5,565,424 A | * | 10/1996 | Gozen et al. | 514/12 |

FOREIGN PATENT DOCUMENTS

| | | |
|---|---|---|
| EP | 0309297 | 3/1989 |
| EP | 0315367 | 5/1989 |
| EP | 0345990 | 12/1989 |
| EP | 0468497 | 1/1992 |
| EP | 0835662 | 4/1998 |
| WO | 9003980 | 4/1990 |
| WO | 9102745 | 3/1991 |
| WO | 9521194 | 8/1995 |
| WO | 0047221 | 8/2000 |

OTHER PUBLICATIONS

Danesi, R., et al., "The Effects of the Somatostatin Analog Octreotide on Angiogensis In Vitro", *Metabolism*, vol. 45, No. 8, Suppl 1, pp 49–50 (Aug. 1996).

Wu, Z., et al., "Suppression of Tumor Growth with Recombinant Murine Angiostatin", *Biochemical and Biophysical Research Communications*, vol. 236, pp 651–654 (1997).
Wiedermann, C.J., et al., "Induction of Endothelial Cell Differentiation into Capillary–Like Structures By Substance P", *European Journal of Pharmacology*, vol. 298, pp 335–338 (1996).
Hanahan, D., et al., Patterns and Emerging Mechanisms of the Angiogenic Switch during Tumorigenesi *Cell*, vol. 86, pp. 353–364 (Aug. 9, 1996).
Minchinton, A.I., et al., "The Effect of Thalidomide on Experimental Tumors and Metastases", *Anti–Cancer Drugs*, vol. 7 pp 339–343 (1996).
Holmgren, L., et al., "Dormancy of Micrometastases: Balanced Proliferation and Apoptosis in the Presen of Angiogenesis Suppression" *Nature Medicine*, vol. 1, No. 2, pp 149–153 (Feb. 1995).
Modzelewski, R.A., et al., "Isolation and Identification of Fresh Tumor–derived Endothelial Cells from a Murine RIF–1 Fibrosarcoma[1]", *Cancer Research*, vol. 54, pp 336–339 (Jan. 15, 1994).
O'Reilly, M.S., et al., "Angiostatin Induces and Sustains Dormancy of Human Primary Tumors in Mice" *Nature Medicine*, vol. 2, No. 6, pp 689–692 (Jun. 1996).
Ziche, M., et al. "Nitic Oxide Mediates Angiogenesis In Vivo and Endothelial Cel Growth and Migratio Vitro Promoted by Substance P" *J. Clin. Invest.*, vol. 94 pp 2036–2044 (Nov. 1994).
Woltering G., et al., "Somatostatin Analogues Inhibit Angiogenesis in the Chick Chorioallantoic Membrane", *Journal of Surgical Research*, vol. 50, No. 3, pp 245–251 (1991).
Kim, Y., et al., Upstream $NF-_kB$ Site is Required for the Maximal Expression of Mouse Inducible Nitric Oxide Synthase Gene in Interferon–y plus Lipopolysaccharide–Induced RAW 264.7 Macrophages *Biochemical and Biophysical Research Communications*, vol. 236, pp 655–660 (1997).
Risau, W., "Mechanisms of Angiogenesis" *Nature*, vol. 386, pp 671–674 (Apr. 17, 1997).
O'Reilly, M.S., et al., "Angiostatin: A Novel Angiogenesis Inhibitor That Mediates the Suppression of Metastases by a Lewis Lung Carcinoma" *Cell*, vol. 79, pp. 315–328 (Oct. 21, 1994).

(List continued on next page.)

*Primary Examiner*—Christopher S. F. Low
*Assistant Examiner*—Abdel A. Mohamed
(74) *Attorney, Agent, or Firm*—Ladas & Parry

(57) ABSTRACT

The invention relates to the use of peptides individually or in combination, for treating and/or preventing angiogenesis. It also relates to the use of peptide analogs or a combination of peptides referred to as MuJ-7 as anticancer drugs in restricting the tumor growth and spread by inhibiting tumor angiogenesis. MuJ-7, in addition inhibits metastasis through its antiangiogenic activity in all cancers. The invention also relates to a pharmaceutical composition containing either individual peptides or in combination, and methods of treatment of human beings and animals for curing and/or preventing angiogenesis.

33 Claims, No Drawings

OTHER PUBLICATIONS

Hu, E., et al., Comparative Studies of the Angiogenic Activity of Vasoactive Intestinal Peptide, Endothelins–1 and 3 and Angiotensin II in a Rat Sponge Model *British Journal of Pharmacology*, vol. 117, pp. 545–551 (1996).

Liebow, C., et al.,"Somatostatin Analogues Inhibit Growth of Pancreatic Cancer By Stimulating Phosphatase." *Proc. Of the Nat. Acad. Of Sciences of the USA*, vol. 86, No. 6 (1989) pp 2003–2007.

Pinski, J., et al. "Inhibition of Growth of MKN45 Human Gastic–Carcinoma Xenografts in Nude Mice by Treatment with Bombesin/Gastrin–Releasing–Peptide Antagonist (RC–3095) and Somatostatin Analogue RC–160." *International Journal of Cancer*, vol. 57, No. 4, pp 574–580 (1994).

Frucht, et al., *Cancer Res.*, vol. 52, No. 5, pp 1114–1122.

E. Bombardieri, et.al., "Somatostatin Receptor Imaging of Small Cell Lung Cancer . . . Scintigraphy," *Journal of Cancer*, vol. 31A, No. 2, pp. 184–188(1995).

J. Pinski, et al., "Somatostatin Analogues and Bombesin/ Gastrin . . . In Vitro and In Vivo," *Peptide Analogues Glioblastomas*, pp. 5895–5901 (1994).

P.A. Bunn, Jr., et al. "Effects of Neuropeptide Analogues on Cancer Cell Lines," *Cancer Research 54*, pp3602–3610 (Jul. 1, 1994).

G. Lilling, et al., "Inhibition of Human Neuroblastoma . . . VIP Antagonist," *Journal of Molecular Neuroscience*, vol. 5, pp. 231–239 (1994/1995).

H. Reile, et al., Characterization of High–Affinity Receptors for Bombesin/Gastrin Releasing . . . By Tumor *The Prostate*, vol. 25, No. 29, p 38 (1994).

I. Virgolini, M.D., et al., "Vasoactive Intestinal Peptide–Receptor . . . Endocrine Tumors," *The New England Jounral of Medicine*, vol. 331, No. 17, pp. 1116–1121 (Oct. 27, 1994).

K. Frank–Raue, et al., "Somatostatin Receptor Imaging In Persistent Medullary Thyroid Carcinoma," *Clinical Endocrinology* vol. 42, pp. 31–37 (1995).

Garbor Halmos, et al., "Characterization of Bombesin/Gastrin–Releasing Peptide . . . Gastric Cancer," *Cancer Letters 85*, pp. 111–118 (1994).

Antal Orosz, et al, "New Short–Chain Analogs of Substance–P . . . Cells In Vitro and In Vivo," *Int. J. Cancer*, vol. 60, pp. 82–87, (1995).

Karoly Szepeshazi, et al., "Combination of Nitrosamine–Induced . . . Bombesin/GRP Antagonist," *Int'l Journal of Pancreatology*, vol. 16, Nos. 2–3, pp. 141–149 (Oct.–Dec. 1994).

P. Heinz–Erian, et al., "Characterization of a New Group of Substituted Substance P . . . Antagonists", *of Papers*, pp. 1455 (May 1986).

Tim Mosmann, "Rapid Colorimetric Assay for Cellular Growth and . . . Cytotoxicity Assays," *Journal of Immunological Methods*, vol. 65, pp. 55–63 (1983).

I. Zachary, et al, "Bombesin, Vasopressin, and Endothelin Rapidly Stimulate . . . 3T3 Cells," *Proc. Natl. Acad. Sci. USA*, vol. 88, pp. 4577–4581 (Jun. 1991).

I. Gozes, et al., "Vasoactive Intestinal Peptide Potentiates Sexual Behavior . . . Antagoinist," *Endocrinology*, vol. 125, No. 6, pp. 2945–2949 (1989).

P.Woll, et al., "[D–ARG$^1$, D–PHE$^5$,D–TRP$^{7,9}$, LEU$^{11}$] Substance P, a Potent Bombesin . . . In Vitro,"*Proc. Natl. Acad. Sci. USA*, vol. 85, pp. 1859–1863 (Mar. 1988).

M. Jaggi, et al., "New, Sensitive and Specific Elisa For Detection . . . Supernatants," *Journal of Immunoassay* vol. 15, No. 2, pp. 129–146 (1994).

K. Gulya, et al., "Cyclic Somatostatin Octapeptide Analogues with High . . . Opoid Receptors," *Life Sciences*, vol., 38, No. 24, pp. 2221–2229 (1968).

M. Brown, et al., "Somatostatin: Analogs with Selected Biological Activities," *Sciences*, vol. 196, pp. 1467–1469, (1977).

J.T. Pelton, et al., "Design and Synthesis of Conformationally Constrained Somatostatin . . . Receptors," *J. Med. Chem.*, vol. 29, pp. 2370–2375 (1986).

M. Jaggi, et al., "Establishment of Tumorigenic Cell Lines from Biopsies . . . Adenocarcinomas," *Journal of Basic and applied Biomedicine*, vol. 3, No. 4, pp. 27–35 (1995).

Barrie, R., et al. "Inhibition of Angiogenesis by Somatostatin and Somatostatin–like Compounds Is Structurally Dependent" *J. Surgical Research*, vol. 55, pp. 446–450, (1993).

Woltering, E.A., et al. "Somatostatin Analogs: Angiogenesis Inhibitors with Novel Mechanisms of Action" *Investigational New Drugs*, vol. 15, pp. 77–86, (1997).

Distrutti, E. et al. "Bombesin (BB) Stimulates Angiogenesis in Large Mammalian Pancreas and MAPK Activity...Cells" *Gastroenterology*, vol. 114, No. 4, Part2, p. A453, (1998).

Fan, T.D., et al. "Stimulation of Angiogenesis by Substance P and Interleukin–1 in the Rat and its Inhibition by NK1...Antagonists" *British J. Pharmacology*, vol. 110, pp. 43–49, (1993).

* cited by examiner

```
                              SEQUENCE LISTING

<160> NUMBER OF SEQ ID NOS: 25

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 1

Lys Pro Arg Arg Pro Tyr Thr Asp Asn Tyr Thr Arg Leu Arg Lys Gln
 1               5                  10                  15

Met Ala Val Lys Lys Tyr Leu Asn Ser Ile Leu Asn
            20                  25

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.

<400> SEQUENCE: 2

Leu Met Tyr Pro Thr Tyr Leu Lys
 1               5

<210> SEQ ID NO 3
<211> LENGTH: 28
<212> TYPE: PRT
<213> ORGANISM: Artificial Sequence
<220> FEATURE:
<221> NAME/KEY: MOD_RES
<222> LOCATION: (6)
<223> OTHER INFORMATION: /product=4-chloro-D-phenylalanine/label=
      4-Cl-D-Phe
<220> FEATURE:
<223> OTHER INFORMATION: Description of Artificial Sequence: This
      peptide was synthetically generated.

<400> SEQUENCE: 3

His Ser Asp Ala Val Xaa Thr Asp Asn Tyr Thr Arg Leu Arg Lys Gln
```

```
        1               5              10              15
Leu Ala Val Lys Lys Tyr Leu Asn Ser Ile Leu Asn
                20              25
```

<210> SEQ ID NO 4
<211> LENGTH: 8
<212> TYPE: PRT
<213> ORGANISM: Artificial Sequence
<220> FEATURE:
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (4)
<223> OTHER INFORMATION: /product=D-tryptophan/label=D-Trp
<220> FEATURE:
<221> NAME/KEY: MOD_RES
<222> LOCATION: (5)
<223> OTHER INFORMATION: /product=ornithine/label=orn
<220> FEATURE:
<221> NAME/KEY: MOD_RES
<222> LOCATION: (7)
<223> OTHER INFORMATION: /product=penicillamine/label=pen
<220> FEATURE:
<223> OTHER INFORMATION: Description of Artificial Sequence: This
      peptide was synthetically generated.

<400> SEQUENCE: 4

```
Xaa Cys Tyr Xaa Xaa Thr Xaa Thr
 1               5
```

<210> SEQ ID NO 5
<211> LENGTH: 14
<212> TYPE: PRT
<213> ORGANISM: Artificial Sequence
<220> FEATURE:
<221> NAME/KEY: MOD_RES
<222> LOCATION: (8)
<223> OTHER INFORMATION: /product=D-tryptophan/label=D-Trp
<220> FEATURE:
<221> NAME/KEY: MOD_RES
<222> LOCATION: (13)..(14)
<223> OTHER INFORMATION: /product=Note:disulfide bridge: 3-14
<220> FEATURE:
<221> NAME/KEY: MOD_RES
<222> LOCATION: (14)
<223> OTHER INFORMATION: /product=D-cysteine/label=D-Cys
<220> FEATURE:
<223> OTHER INFORMATION: Description of Artificial Sequence: This
      peptide was synthetically generated

<400> SEQUENCE: 5

```
Ala Gly Cys Lys Asn Phe Phe Xaa Lys Thr Phe Thr Ser Xaa
 1               5                  10
```

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (8)
<223> OTHER INFORMATION: /product=leucine N-ethylamide/label=Leu-NHEt

<400> SEQUENCE: 6

```
Xaa Gln Trp Ala Val Gly His Xaa
 1               5
```

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-arginine/label=D-Arg
<220> FEATURE:
<221> NAME/KEY: MOD_RES
<222> LOCATION: (5)
<223> OTHER INFORMATION: /product=D-phenylalanine/label=D-Phe
<220> FEATURE:
<221> NAME/KEY: MOD_RES
<222> LOCATION: (7)
<223> OTHER INFORMATION: /product=D-tryptophan/label=D-trp
<220> FEATURE:
<221> NAME/KEY: MOD_RES
<222> LOCATION: (9)
<223> OTHER INFORMATION: /product=D-tryptophan/label=D-Trp
<220> FEATURE:
<221> NAME/KEY: MOD_RES
<222> LOCATION: (11)
<223> OTHER INFORMATION: /product=leucine N-ethylamide/label=Leu-NHEt

<400> SEQUENCE: 7

```
Xaa Pro Lys Pro Xaa Gln Xaa Phe Xaa Leu Xaa
 1               5                  10
```

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=2-amino-isobutyric acid/label=Aib
<220> FEATURE:
<221> NAME/KEY: MOD_RES
<222> LOCATION: (7)
<223> OTHER INFORMATION: /product=2-amino-isobutyric acid/label=Aib

<400> SEQUENCE: 8

```
Xaa Met Tyr Pro Thr Tyr Xaa Lys
 1               5
```

<210> SEQ ID NO 9
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-leucine/label=D-Leu
<220> FEATURE:
<221> NAME/KEY: MOD_RES
<222> LOCATION: (7)
<223> OTHER INFORMATION: /product=2-amino-isobutyric acid/label=Aib

<400> SEQUENCE: 9

```
Xaa Met Tyr Pro Thr Tyr Xaa Lys
  1               5
```

```
<210> SEQ ID NO 10
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (6)
<223> OTHER INFORMATION: /product=D-tyrosine/label=D-Tyr

<400> SEQUENCE: 10
```

```
Leu Met Tyr Pro Thr Xaa Leu Lys
  1               5
```

```
<210> SEQ ID NO 11
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (7)
<223> OTHER INFORMATION: /product=D-leucine/label=D-Leu

<400> SEQUENCE: 11
```

```
Leu Met Tyr Pro Thr Tyr Xaa Lys
  1               5
```

```
<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (3)
<223> OTHER INFORMATION: /product=D-tyrosine/label=D-Tyr
<220> FEATURE:
<221> NAME/KEY: MOD_RES
<222> LOCATION: (7)
<223> OTHER INFORMATION: /product=D-leucine/label=D-Leu

<400> SEQUENCE: 12
```

```
Leu Met Xaa Pro Thr Tyr Xaa Lys
  1               5
```

```
<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-leucine/label=D-Leu
<220> FEATURE:
<221> NAME/KEY: MOD_RES
<222> LOCATION: (7)
<223> OTHER INFORMATION: /product=D-leucine/label=D-leu

<400> SEQUENCE: 13
```

```
Xaa Met Tyr Pro Thr Tyr Xaa Lys
 1               5
```

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=2-amino-isobutyric acid/label=Aib
<220> FEATURE:
<221> NAME/KEY: MOD_RES
<222> LOCATION: (7)
<223> OTHER INFORMATION: /product = Diethyl glycine/label=Deg

<400> SEQUENCE: 14

```
Xaa Met Tyr Pro Thr Tyr Xaa Lys
 1               5
```

<210> SEQ ID NO 15
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-leucine/label=D-leu
<220> FEATURE:
<221> NAME/KEY: MOD_RES
<222> LOCATION: (7)
<223> OTHER INFORMATION: /product= Diethyl glycine/label=Deg

<400> SEQUENCE: 15

```
Xaa Met Tyr Pro Thr Tyr Xaa Lys
 1               5
```

<210> SEQ ID NO 16
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-phenylalanine/label=D-Phe;
<220> FEATURE:
<221> NAME/KEY: MOD_RES
<222> LOCATION: (4)
<223> OTHER INFORMATION: /product=2-amino-isobutyric acid/label=Aib

<400> SEQUENCE: 16

```
Xaa Gln Trp Xaa Val Gly His Leu
 1               5
```

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:

```
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (6)
<223> OTHER INFORMATION: /product=2-amino-isobutyric acid/label=Aib

<400> SEQUENCE: 17

Xaa Gln Trp Ala Val Xaa His Leu
 1               5

<210> SEQ ID NO 18
<211> LENGTH: 8
<212> TYPE: PRT
<213> ORGANISM: Artificial Sequence
<220> FEATURE:
<223> OTHER INFORMATION: Description of Artificial Sequence: This
      peptide was syntetically generated.
<220> FEATURE:
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (4)
<223> OTHER INFORMATION: /product=2-amino-isobutyric acid/label=Aib

<400> SEQUENCE: 18

Xaa Gln Trp Xaa Val Gly His Ile
 1               5

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (6)
<223> OTHER INFORMATION: /product=2-amino-isobutyric acid/label=Aib

<400> SEQUENCE: 19

Xaa Gln Trp Ala Val Xaa His Ile
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=2-amino-isobutyric acid/label=Aib
<220> FEATURE:
<221> NAME/KEY: MOD_RES
<222> LOCATION: (6)
<223> OTHER INFORMATION: /product=2-amino-isobutyric acid/label=Aib

<400> SEQUENCE: 20

Xaa Met Gln Trp Phe Xaa
 1               5
```

```
<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-leucine/label=D-leu
<220> FEATURE:
<221> NAME/KEY: MOD_RES
<222> LOCATION: (6)
<223> OTHER INFORMATION: /product=2-amino-isobutyric acid/label=Aib

<400> SEQUENCE: 21

Xaa Met Gln Trp Phe Xaa
 1               5

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-arginine/label=D-Arg
<220> FEATURE:
<221> NAME/KEY: MOD_RES
<222> LOCATION: (5)
<223> OTHER INFORMATION: /product=2-amino-isobutyric acid/label=Aib
<220> FEATURE:
<221> NAME/KEY: MOD_RES
<222> LOCATION: (7)
<223> OTHER INFORMATION: /product=D-tryptophan/label=D-Trp
<220> FEATURE:
<221> NAME/KEY: MOD_RES
<222> LOCATION: (9)
<223> OTHER INFORMATION: /product=D-tryptophan/label=D-Trp
<220> FEATURE:
<221> NAME/KEY: MOD_RES
<222> LOCATION: (10)
<223> OTHER INFORMATION: /product=2-amino-isobutyric acid/label=Aib

<400> SEQUENCE: 22

Xaa Pro Lys Pro Xaa Gln Xaa Phe Xaa Xaa Leu
 1               5                  10

<210> SEQ ID NO 23
<211> LENGTH: 14
<212> TYPE: PRT
<213> ORGANISM: Artificial Sequence
<220> FEATURE:
<221> NAME/KEY: MOD_RES
<222> LOCATION: (2)
<223> OTHER INFORMATION: /product=2-amino-isobutyric acid/label=Aib
<220> FEATURE:
<221> NAME/KEY: MOD_RES
<222> LOCATION: (8)
<223> OTHER INFORMATION: /product=D-tryptophan/label=D-Trp
<220> FEATURE:
<221> NAME/KEY: MOD_RES
<222> LOCATION: (13)..(14)
<223> OTHER INFORMATION: /product=Note: disulfide bridge:3-14

<400> SEQUENCE: 23

Ala Xaa Cys Lys Asn Phe Phe Xaa Lys Thr Phe Thr Ser Cys
 1               5                  10
```

```
<210> SEQ ID NO 24
<211> LENGTH: 14
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (2)
<223> OTHER INFORMATION: /product=2-amino-isobutyric acid/label=Aib
<220> FEATURE:
<221> NAME/KEY: MOD_RES
<222> LOCATION: (8)
<223> OTHER INFORMATION: /product=D-tryptophan/label=D-Trp

<400> SEQUENCE: 24

Ala Xaa Cys Lys Asn Phe Phe Xaa Lys Thr Phe Thr Ser Cys
 1               5                  10

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: This
      peptide was synthetically generated.
<220> FEATURE:
<221> NAME/KEY: MOD_RES
<222> LOCATION: (1)
<223> OTHER INFORMATION: /product=D-phenylalanine/label=D-Phe
<220> FEATURE:
<221> NAME/KEY: MOD_RES
<222> LOCATION: (4)
<223> OTHER INFORMATION: /product=D-tryptophan/label=D-Trp
<220> FEATURE:
<221> NAME/KEY: MOD_RES
<222> LOCATION: (7)
<223> OTHER INFORMATION: /product=2-amino-isobutyric acid/label=Aib

<400> SEQUENCE: 25

Xaa Cys Tyr Xaa Lys Thr Xaa Thr
 1               5
```

ANTIANGIOGENIC DRUGS

This application is a continuation-in-part of application No. 08/727,679 filed on Oct. 8, 1996 now U.S. Pat. No. 6,156,725 and claims benefit of Ser. No. 60/080,433 filed Apr. 2, 1998.

FIELD OF INVENTION

The invention relates to the use of peptides individually or in combination, for treating and/or preventing angiogenesis. It also relates to the use of a combination of peptides referred to as MuJ-7 as an anticancer drug in restricting tumor growth and its spread by inhibiting tumor angiogenesis. MuJ-7, in addition inhibits metastasis through its antiangiogenic activity in all cancers. The invention also relates to a pharmaceutical composition containing either individual peptides or combinations of peptides, and methods of treatment of human beings and animals for curing and/or preventing angiogenesis.

BACKGROUND OF THE INVENTION

Angiogenesis is the growth of new microvessels. This process depends mainly on locomotion, proliferation, and tube formation by capillary endothelial cells. During angiogenesis, endothelial cells emerge from their quiescent state and can proliferate as rapidly as bone marrow cells, but unlike the bone marrow, angiogenesis is usually focal and of brief duration. Pathologic angiogenesis, while still a focal process, persists for months or years. The angiogenesis that occurs in diseases of ocular neovascularisation, arthritis, skin diseases, and tumors rarely terminates spontaneously and has until recently, been difficult to suppress therapeutically. Therefore, the fundamental goal of all antiangiogenic therapy is to return foci of proliferating microvessels to their normal resting state, and to prevent their regrowth[1].

Although the molecular mechanisms responsible for transition of a cell to angiogenic phenotype are not known, the sequence of events leading to the formation of new vessels has been well documented[2,3]. The vascular growth entails either endothelial sprouting[3,4] or intussusception[5]. In the first pathway, the following sequence of events may occur: (a) dissolution of the basement of the vessel, usually a postcapillary venule, and the interstitial matrix; (b) migration of endothelial cells toward the stimulus; (c) proliferation of endothelial cells trailing behind the leading endothelial cell(s); (d) formation of lumen (canalization) in the endothelial array/sprout; (e) formation of branches and loops by confluence/anastomoses of sprouts to permit blood flow; (f) investment of the vessel with pericytes; and (g) formation of basement membrane around the immature vessel[2,3]. New vessels can also be formed via the second pathway: insertion of interstitial tissue columns into the lumen of preexisting vessels. The subsequent growth of these columns and their stabilization result in partitioning of the vessel lumen and remodelling of the local vascular network[5,6].

The rationale for antiangiogenic therapy is that progressive tumor growth is angiogenesis-dependent[8]. The switch to the angiogenic phenotype appears to be an independent event that occurs during the multistage progression to neoplasia[9]. The angiogenic switch itself, while relatively sudden and well localized, is nonetheless a complex process. This phenotype is currently understood in terms of a shift in the net balance of stimulators and inhibitors of angiogenesis, during which inhibitors are down regulated[10,11].

Once new capillary loops converge toward a small in situ carcinoma or a microscopic metastasis, the tumor cells are bathed in additional survival factors and growth factors, not only from the circulating blood (perfusion effect) but also from vascular endothelial cells themselves (paracrine effect). The positive regulators of angiogenesis include at least 14 angiogenic proteins that have been discovered during the past 12 years and which have been sequenced and cloned[12]. Basic fibroblast growth factor (bFGF) and vascular endothelial growth factor (VEGF) are the most well studied and are found in a majority of different types of human tumors. During the angiogenic switch one or more of these angiogenic stimulators is upregulated and it appears, however, that this up regulation of angiogenic stimulators is accompanied by down regulation of local tissue inhibitors of angiogenesis.

The paracrine stimulation of tumor cells by products from endothelial cells also operates in the other direction. Endothelial cell survival and growth are driven by tumor derived mitogens and motogens. These findings have led to a model of tumor growth in which the endothelial cell compartment and the tumor cell compartment interact with each other. They not only stimulate each other's growth, but if the endothelial cells are made unresponsive to angiogenic stimuli from the tumor cells, by administration of a specific endothelial inhibitor, both primary tumors[11] and metastatic tumors[10] can be held dormant, at a microscopic size. One could take advantage of this difference between endothelial cells and tumor cells by administering an angiogenesis inhibitor together with conventional cytotoxic chemotherapy up to the point at which the cytotoxic therapy would normally be discontinued because of toxicity or drug resistance. The angiogenesis inhibitor(s) could then be continued (for years), to maintain either stable disease or tumor dormancy[1]. Such combinations of antiangiogenic and cytotoxic therapy in tumor-bearing animals have been curative, whereas either agent alone is merely as inhibitor[15].

Peptides/Proteins have previously been studied for antiangiogenic activity. Thrombospondin-1 (TSP-1) which is a naturally occurring inhibitor of angiogenesis, makes endothelial cells unresponsive to a wide variety of inducers. Both native TSP-1 and small antiangiogenic peptides derived from it show that this inhibition is mediated by CD36[16] (Dawson et al., 1997). Both IgG antibodies against CD36 and glutathione-S-transferase-CD36 fusion proteins that contain the TSP-1 binding site blocked the ability of intact TSP-1 and its active peptides to inhibit the migration of cultured microvascular endothelial cells.

The family of tissue inhibitors of metalloproteinases (TIMPs) are known to be specific inhibitors of matrix metalloproteinases (MMPs). The local balance between MMPs and TIMPs is believed to play a major role in extracellular matrix (ECM) remodelling during diseases such as cancer. TIMP-3 which is unique in being a component of ECM, inhibits endothelial cell migration and tube formation in response to angiogenic factors[17] (Anand-Apte et al., 1996).

The conditioned medium of human promyelocytic leukemia (HL6O) cells has been shown to contain a cell growth inhibitory factor, human cytostatin. Human cytostatin can inhibit endothelial cell proliferation, migration and microvessel tube formation on Matrigel-coated surfaces[18] (Yeung AK et al., 1996). Furthermore the anti-angiogenic effect of human cytostatin has been demonstrated on the chick chorioallantoic membrane. Human cytostatin can inhibit new blood vessel development, but cannot regress existing blood vessels.

Angiostatin, which is a 38 kD internal fragment of plasminogen is an antiangiogenic endothelial cell inhibitor and suppresses the growth of primary Lewis lung carcinoma in vivo[19] (Wu, Z. et al., 1997).

Thalidomide has recently been shown to antagonize basic fibroblast growth factor-induced angiogenesis in the rat corneal micropocket assay. It has been suggested that thalidomide elevates tumor hypoxia in the Lewis lung tumor, presumably via an antiangiogenic mechanism[20] (Minchinton AI et al., 1996).

One study examined the in vitro antiangioegneic effects of the somatostatin analog octreotide on the growth of human umbelical vein endothelial cells (HUVEC) and vascular cells from explants of rat aorta cultured on fibronectin-coated dishes or included in fibrin gel. A total $10^{-9}M$ octreotide reduced the mean uptake of $^3H$-thymidine by HUVEC cells by 37% compared with controls. The $10^{-8M}$ concentration of octreotide inhibited the proliferation of endothelial and smooth muscle cells growing on fibronectin by 32.6% and reduced the sprouting of cells from the adventitia of aortic rings in fibrin by 33.2% compared with controls, as measured by tetrazolium bioreduction and image analysis, respectively. These results demonstrate that octreotide is an effective inhibitor of vascular cell proliferation in vitro[21] (Danesi R. Del Taccam, Metabolism August 1996. 45(8 Supp 1: 49–50). In another experiment, somatostatin analogs SMS 201-995 and RC-160 were found to inhibit angiogenesis in the chick chorioallantoic membrane of the developing chicken embryo. Somatostatin analogues were associated in a dose-related fashion with both a greater percentage of inhibition of blood vessel growth and an increased grade of inhibition. It was hypothesized that inhibition of angiogenesis may be a mechanism responsible for the tumor regression observed in vivo following SMS or RC-160 therapy[22] (Woltering E A et al., J. Surg. Res. March 1991, 50(3): 245–251).

The proinflammatory neuropeptide, substance P, stimulated angio-genesis in an in vitro model using HUVECs cultured on a basement membrane (Matrigel) substrate. Substance P stimulated endothelial cell differentiation into capillary-like structures in a dose-dependent manner. Stimulation of endothelial cell differentiation is a newly recognized biological function of substance P[23] (Wiedermann, C. J. et al. Eur. J. Pharmacol. Mar. 18, 1996, 298 (3): 335–338).

The effects of Nitric oxide (NO) generation and endogenous production of NO elicited by substance P (SP) in angiogenic process were evaluated in the rabbit cornea (in vivo) and by measuring growth and migration of endothelial cells (in vitro). The NO synthase inhibitors given systemically inhibited angiogenesis elicited by [sar9]-SP-Sulfone. Capillary endothelial cell proliferation and migration produced by SP were abolished by pretreatment with the NO synthase inhibitors. Exposure of the cells to SP activated the calcium-dependent NO synthase. These data indicate that NO production induced by vasoactive agents, such as SP, functions as an autocrine regulator of the microvascular events necessary for neovascularization and mediates angiogenesis[24] (Ziche M. et al., J. Clin. Invest. November 1994, 94(5):2036–2044).

The angiogenic activity of four vasoactive peptides with a range of vasodilator and vasoconstrictor properties were investigated in a rat sponge model. 2 daily doses of vasodilator peptide VIP(10 pmol) when given with interleukin-1 alpha caused intense neovascularization which was inhibited by simultaneous administration of VIP(10-28), a specific VIP receptor antagonist. These data show that VIP possesses angiogenic activity and the blockade of VIP induced angiogenesis at the receptor level could provide a strategy for the management of angiogenic disease[25].

Vascular endothelial cells are important in a variety of physiological and pathophysiological processes. The growth and functions of vascular endothelial cells are regulated both by soluble mitogenic and differentiation factors and by interactions with the extracellular matrix; however, relatively little is known about the role of the matrix. The neuropeptide bombesin, the bioactive lipid lysophosphatidic acid (LPA), and the cytokine tumor necrosis factor alpha, which signal through diverse mechanisms, were all able to activate MAPK to a much greater degree in fibronectin adherent cells than in suspended cells. Together, these data suggest a cooperation between integrins and soluble mitogens in efficient propagation of signals to downstream kinases. This cooperation may contribute to anchorage dependence of mitogenic cell cycle progression (Short S M et al, Molecular Biology of the Cell 9(8):1969–1980, 1998).

Cell adhesion to the extracellular matrix (ECM) has been implicated in apoptosis in anchorage-dependent cell types. It was recently found that a peptide derived from fibronectin (termed III14-2) inhibits the integrin-mediated cell adhesion to ECM. Using this antiadhesive peptide and a variety of ECM proteins, a critical role of the integrin-ECM protein interaction in apoptotic regulation of human umbilical vein endothelial cells (HUVEC) has been demonstrated. HUVEC in suspension undergoes apoptosis under the serum-free conditions, as judged by nuclear and DNA fragmentations (Fukai F et al, Experimental Cell Research, 242(l):92–99, 1998).

It has been previously shown that vasoactive intestinal polypeptide (VIP) induces endothelium-dependent relaxation of the human uterine artery. Non-competitive antagonism with methylene blue revealed that the pKa value for VIP-receptor complex was 8.10+/−0.10 (n=6) and the receptor reserve expressed as K-A/EC50 was 0.89+/−0.11, where pKa=log (10)K(A), and K-A is the dissociation constant of VIP-receptor complex (Jovanovic A. et al. Molecular Human Reproduction, 4(1):71–76, 1998).

Somatostatin (SRIF) exerts antiproliferative effects, and has recently been evaluated in clinical trials for the prophylaxis of restenosis following coronary angioplasty. 3 SRIF (0.1–1000 nM) caused a concentration-dependent inhibition of the bFGF-stimulated regrowth in CHO-K1 cells expressing human sst(2) (h sst(2)) or sst(5) (h sst(5)) receptors (pIC(50)=8.05+/−0.03 and 8.56+/−0.12, respectively). SRIF (0.1–1000 nM) was able to inhibit the bFGF-stimulated re-growth (pIC(50)=7.98+/−24 and 8.50+/−0.12, respectively). (Alderton F et al, British Journal of Pharmacology, 124(2): 323–330, 1998).

Substance P (SP) was analyzed in rat brain endothelium cultures after cytokine stimulation. SP secretion was found after stimulation with high doses of interleukin-l beta (IL-1 beta) and tumor necrosis factor alpah (TNF-alpha). Under cytokine stimulation, part of SP was bound to brain endothelial cell surface, suggesting the existence of an autocrine network for this neuropeptide. SP regulates cellular processes in the CNS, placenta and vasculature include permeability, inflammation, mitogenesis and transformation. Increased SPR mRNA level in response to E-2 were linearly related to increased [H-3]SP binding to the SPR (Villablanca A C et al, Molecular & Cellular Endocrinology, 135(2):109–117, 1997).

SUMMARY OF INVENTION

The present invention provides pharmaceutical compositions for treating cancer angiogenesis and cancer metastasis. The invention provides a method of treating angiogenesis, cancer and cancer metastasis employing a pharmaceutically effective dosage of a combination of peptides or individual peptides. It is an object of this invention that a combination of peptides used is known as MuJ-7. Individual constituent peptides of MuJ-7 and pharmaceutically acceptable additives can be used. The present invention provides a pharmaceutical composition useful for killing or inhibiting multiplication of tumor cells as well as cancer cells. The pharmaceutical composition may also be useful in preventing, inhibiting, or modulating the hypersecretion of VIP, somatostain, bombesin, Substance P, or a combination of VIP, somatostatin, bombesin, or Substance P.

The composition may suitably comprise, consist of, or consist essentially of a therapeutically effective combination of peptide analogs of somatostatin, VIP, bombesin, and Substance P. The peptide analogs are described in more detail below, but constituents functionally interchangeable with those specifically described may also be employed in the claimed pharmaceutical composition. More particularly, the pharmaceutical composition may suitably comprise, consist of, or consist essentially of an analog of somatostatin and at least four peptides selected from the group consisting of a first analog of VIP, a second analog of VIP, a third analog of VIP, analog of somatostatin another analog of somatostatin, an analog of bombesin, and an analog of Substance P. More particularly, the composition may suitably comprise, consist of, or consist essentially of a therapeutically effective combination of peptide $SOM_2$ (an analog of somatostatin) and at least four of the following peptides: $VIP_1$ (a VIP anatagonist), $VIP_2$ (a VIP) receptor binding inhibitor), $VIP_3$ (a VIP receptor antagonist), $SOM_1$ (a somatostatin analog (also abbreviated "CTOP." which is derived from the first letters of the following four amino acids: $Cys^2$, Tyr, $Orn^5$, and $Pen^5$), $BOM_1$ (a bombesin antagonist), and $SP_1$ (a Substance P antagonist). In a preferred embodiment, a pharmaceutically acceptable carrier, diluent, or solvent is used. The invention provides a method of treatment for humans, mammals, or other animals suffering from cancer or other tumors. The invention also provides a method of treatment for humans, mammals, or other animals suffering from hypersecretion of VIP, somatostatin, bombesin, Substance P, or a combination of VIP, somatostatin, bombesin, or Substance P. The method may suitably comprise, consist of, or consist essentially of administering a therapeutically effective dose of the pharmaceutical composition so as to prevent, inhibit, or modulate the hypersecretion of VIP, somatostatin, bombesin, Substance P, or a combination of VIP, somatostatin, bombesin, or Substance P.

In addition, the compositions may comprise, consist essentially of or consist of one or more of peptides identified below as DT-11; DT-12; DT-13; DT-14; DT-15; DT-16; DT-18; DT-19; DT-23; DT-24; DT-26; DT-27; DT-31; DT-33; DT-34; DT-62A; DT-62B; DT-71 which are peptide analogs.

DETAILED DESCRIPTION

We have observed that VIP (vasoactive intestinal peptide), somatostatin, substance P, and bombesin are secreted by at least some human tumor and cancer cells and that there are binding sites for these peptides on these cells. Specifically, out of a number of peptide growth regulators studied by indirect immunofluorescence, the four peptides (i.e., vasoactive intestinal peptide (VIP), somatostatin, Substance P, and bombesin) were shown to bind, to tumor cells. (Herein, the terms "peptide growth regulators", and "peptides" each refer to VIP, somatostatin, Substance P, and bombesin). It may be that there is an autocrine mechanism for cell proliferation where the peptides are secreted by tumor cells and transduce a signal through specific receptors on the same cell type leading to cell proliferation. As will be described in more detail below, the effects of the analogs of somatostatin, VIP, bombesin, Substance P on the tumor cell growth and survival were studied using different assay systems. The amino-acid sequences of the seven analogs ($VIP_1$, $VIP_2$, $VIP_3$, $SOM_1$, $SOM_1$, $BOM_2$ and $SP_1$) are disclosed in U.S. application Ser. No. 08/727,679.

| Code | Name | Sequence | SEQ ID NO: |
|---|---|---|---|
| $VIP_1$ | VIP antagonist | (Lys-Pro-Arg-Arg-Pro-Tyr-Thr-Asp-Asn-Tyr-Thr-Arg-Leu-Arg-Lys-Gln-Met-Ala-Val-Lys-Lys-Tyr-Leu-Asn-Ser-Ile-Leu-Asn-$NH_2$) | SEQ ID NO: 1 |
| $VIP_2$ | VIP receptor binding inhibitor | (Leu-Met-Tyr-Pro-Thr-Tyr-Leu-Lys) | SEQ ID NO: 2 |
| $VIP_3$ | VIP receptor antagonist | (His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-$NH_2$) | SEQ ID NO: 3 |
| $SOM_1$ | Somatostatin analog (CTOP) | D-Phe-Cys-Tyr-D-Trp-Orn-Thr-Pen-Thr-$NH_2$ | SEQ ID NO: 4 |
| $SOM_2$ | Somatostatin analog | Ala-Gly-Cys-Lys-Asn-Phe-Phe-D-Trp-Lys-Thr-Phe-Thr-Ser-D-Cys (disulfide bridges: 3–14) | SEQ ID NO: 5 |
| $BOM_1$ | Bombesin antagonist | D-Phe-Gln-Trp-Ala-Val-Gly-His-Leu-NHEt | SEQ ID NO: 6 |
| $SP_1$ | Substance P antagonist | D-Arg-Pro-Lys-Pro-D-Phe-Gln-D-Trp-Phe-D-Trp Leu-Leu-$NH_2$ | SEQ ID NO: 7 |

As will be explained in more detail below, the combination of these seven analogs is known as MuJ-7. The analogs were synthesized manually and using a conventional peptide synthesizer. An example of a combination within the scope of the invention comprises $SOM_2$, $VIP_1$, $VIP_2$, $VIP_3$, $SOM_1$, $BOM_1$, and $SP_1$. A combination hereinafter referred to as MuJ-7, was prepared using the following seven peptide analogs: (1) $VIP_1$, (the VIP antagonist) having a molecular weight of approximately 3464.9 and a concentration of approximately $10^{-7}$ M; (2) $VIP_2$. (the receptor binding inhibitor) having a molecular weight of approximately 1027.55 and a concentration of approximately $10^{-8}$M; (3) VIP$_3$, (the VIP receptor antagonist) having a molecular weight of approximately 3342.09 and a concentration of approximately $10^{-8}$M; (4) SOM$_1$ (the somatostatin analog (CTOP) having a molecular weight of approximately 1061.59 and a concentration of approximately $10^{-9}$M; (5) SOM$_2$, (the analog of somatostatin) having a molecular weight of approximately 1637.0 and a concentration of approximately $10^{-8}$M; (6) BOM$_1$ (the bombesin antagonist) having a molecular weight of approximately 983.55 and a concentration of approximately $10^{-8}$M; and (7) SP$_1$ (the Substance P antagonist) having a molecular weight of approximately 1515.83 and a concentration of approximately $10^{-8}$M. The preceding sentence sets forth the preferred concentrations of the seven analogs comprising MuJ-expected that MuJ-7 would be effective if the concentration of each of the seven analogs ranged from approximately $10^{-6}$M to approximately $10^{-12}$M.

MuJ-7 may be prepared in the following way. A stock solution of each of the seven peptide analogs is prepared with a pH of approximately 7.0 to approximately 7.4. Although sterile phosphate buffered saline was used to prepare the stock solutions for the testing described below, other diluents may be used such as RPMI 1649, buffered saline, isotonic NaCl, Ringer's solution, water (for injection) distilled water, polyethylene glycol (near or in water), 2% Tween in water, dimethylsulfoxide to 50% in water, propylene glycol (neat or in water), balanced salt solution, glycerol, and other conventional fluids that are suitable for intravenous administration to obtain a pH in the range of approximately 7.0 to approximately 7.4 for each stock solution, the pH can be adjusted by using 1 N HCl for lowering the pH or 1 N NaOH for raising the pH, although the conventional agents for adjusting the pH can be used, the concentration of the peptide analog in each stock solution is approximately $10^{-3}$M.

Aliquots of the seven peptides analogs are mixed together such that the MuJ-7 formulation contained approximately equal weights of each of the seven peptide analogs. In MuJ-7, approximately, the concentration of VIP$_1$, is $10^{-7}$M; the concentration of VIP$_2$ is $10^{-8}$M; the concentration of VIP$_3$ is $10^{-8}$M; the concentration of SOM1 is $10^{-9}$M; the concentration of SOM$_2$ is $10^{-8}$M; the concentration of BOM1 is $10^{-8}$M; and the concentration of SP$_1$ is $10^{-8}$M. In one exemplary embodiment, the pH of the MuJ-7 solution may range from about 7.0 to 7.4. To obtain a pH in this range, the pH can be adjusted by using 1 N NCl for lowering the pH or 1 N NaOH for raising the pH, although other conventional agents for adjusting the pH can be used.

In addition, a number of novel peptides also exhibited an antiangiogenic effect. These peptides are:

| DT-11 | Aib-Met-Tyr-Pro-Thr-Tyr-Aib-Lys-OH | (SEQ ID NO: 8) |
| DT-12 | D-Leu-Met-Tyr-Pro-Thr-Tyr-Aib-Lys-OH | (SEQ ID NO: 9) |
| DT-13 | Leu-Met-Tyr-Pro-Thr-D-Tyr-Leu-Lys-OH | (SEQ ID NO: 10) |
| DT-14 | Leu-Met-Tyr-Pro-Thr-Tyr-D-Leu-Lys-OH | (SEQ ID NO: 11) |
| DT-15 | Leu-Met-D-Tyr-Pro-Thr-Tyr-D-Leu-Lys-OH | (SEQ ID NO: 12) |
| DT-16 | D-Leu-Met-Tyr-Pro-Thr-Tyr-D-Leu-Lys-OH | (SEQ ID NO: 13) |
| DT-18 | Aib-Met-Tyr-Pro-Thr-Tyr-Deg-Lys-OH | (SEQ ID NO: 14) |
| DT-19 | D-Leu-Met-Tyr-Pro-Thr-Tyr-Deg-Lys-OH | (SEQ ID NO: 15) |

-continued

| DT-23 | D-Phe-Gln-Trp-Aib-Val-Gly-His-Leu-NH$_2$ | (SEQ ID NO: 16) |
| DT-24 | D-Phe-Gln-Trp-Ala-Val-Aib-His-Leu-NH$_2$ | (SEQ ID NO: 17) |
| DT-26 | D-Phe-Gln-Trp-Aib-Val-Gly-His-Ile-NH$_2$ | (SEQ ID NO: 18) |
| DT-27 | D-Phe-Gln-Trp-Ala-Val-Aib-His-Ile-NH$_2$ | (SEQ ID NO: 19) |
| DT-31 | Aib-Met-Gln-Trp-Phe-Aib-NH$_2$ | (SEQ ID NO: 20) |
| DT-33 | D-Leu-Met-Gln-Trp-Phe-Aib-NH$_2$ | (SEQ ID NO: 21) |
| DT-34 | D-Arg-Pro-Lys-Pro-Aib-Gln-D-Trp-Phe-D-Trp-Aib-Leu-NH$_2$ | (SEQ ID NO: 22) |
| DT-62A | Ala-Aib-Cys-Lys-Asn-Phe-Phe-D-Trp-Lys-Thr-Phe-Thr-Ser-Cys (3–14 Disulphide bond) | (SEQ ID NO: 23) |
| DT-62B | Ala-Aib-Cys-Lys-Asn-Phe-Phe-D-Trp-Lys-Thr-Phe-Thr-Ser-Cys | (SEQ ID NO: 24) |
| DT-71 | D-Phe-Cys-Tyr-D-Trp-Lys-Thr-Aib-Thr-NH$_2$ | (SEQ ID NO: 25) |

MuJ-7 was tested against primary tumor cells of human colon adenocarcinoma, and each of the peptide analogs comprising MuJ-7 was tested individually against human colon adenocarcinoma cells. A three day MTT cytotoxicity assay was performed as described in U.S. patent application Ser. No. 08/727,679. The percent killing achieved by individual peptides was in the range of 54 to 79% while percent killing achieved by MuJ-7 was 94%.

Five different subcombinations of seven peptide analogs comprising MuJ-7 were tested against human colon adenocarcinoma cells. Each subcombination was tested by performing a one day MTT cytotoxicity assay as described in U.S. patent application Ser. No. 08/727,679. The percent killing achieved by the subcombinations was in the range of 64.7% to 94.9%.

EXAMPLE 1

ECV.304 cells collected at exponential growth phase were resuspended in medium ($3.3\times10^6$ cells/ml in RPMI 1640 containing 10% FBS). 150 $\mu$l of medium was added to the wells of a 96-well tissue culture plate (Nunc, Denmark) followed by 30 $\mu$l of cell suspension. The plate was left in incubator (37° C., 5% CO$_2$) overnight. Each of the seven peptides of the combination MuJ-7 were added at three molar concentrations of $10^{-7}$M, $10^{-8}$M and $10^{-9}$M. 20 $\mu$l of MuJ-7 at three concentrations of N/10, N and 10N was added to marked wells of the 96-well plate. The value of N for each of the individual peptides was $10^{-8}$M for VIP$_2$, BOM$_1$, SP$_1$, VIP$_3$, and SOM$_2$ and $10^{-7}$M for VIP$_1$, and $10^{-9}$M for SOM$_1$. Each concentration was plated in triplicate. 20 $\mu$l of medium alone was added to control wells while wells without cells served as blanks. A total volume of 200 $\mu$l was ensured in each well and the plate was left in an incubator (37° C., 5% CO$_2$). After 72 hours of incubation an MTT assay was performed and percentage inhibition in proliferation of treated cells was calculated with respect to control cells. Results are given in Table I.

TABLE 1

Percent inhibition in proliferation of endothelial cells on treatment with different concentrations of MuJ-7 and its constituent peptides.

| | Percent Inhibition Proliferation (%) | | | | | | | | | | | | | | | | | | | | | |
|---|---|---|---|---|---|---|---|---|---|---|---|---|---|---|---|---|---|---|---|---|---|---|
| | $VIP_2$ | | | $BOM_1$ | | | $SP_1$ | | | $VIP_1$ | | | $VIP_3$ | | | $SOM_2$ | | | $SOM_1$ | | | MuJ-7 | |
| Cell line | −7 | −8 | −9 | −7 | −8 | −9 | −7 | −8 | −9 | −7 | −8 | −9 | −7 | −8 | −9 | −7 | −8 | −9 | −7 | −8 | −9 | N/10 | N | 10N |
| EaHy.926 | 32 | 28 | 42 | 38 | 31 | 32 | 49 | 32 | 37 | 25 | 24 | 23 | 21 | 9 | 24 | 36 | 38 | 25 | 36 | 36 | 22 | 36 | 44 | 38 |
| ECV.304 | 24 | 25 | 22 | 21 | 22 | 19 | 18 | 24 | 22 | 15 | 17 | 16 | 21 | 25 | 22 | 20 | 19 | 17 | 20 | 20 | 19 | 24 | 31 | 28 |

EXAMPLE 2

ECV304 cells collected at exponential growth phase were resuspended in medium ($3.3 \times 10^6$ cells/ml in RPMI 1640 containing 10% FBS). 150 μl of medium was added to the wells of a 96-well tissue culture plate (Nunc, Denmark) followed by 30 μl of cell suspension. The plate was left in incubator (37° C., 5% $CO_2$) overnight. Novel peptides shown below were incubated with cells at concentration range of $10^{-7}$ to $10^{-9}$ M (except DT71 at concentration range $10^{-8}$ to $10^{-10}$ M). Each concentration was plated in triplicates. 20 μl of medium alone was added to control wells while wells without cells served as blanks. A total volume of 200 μl was ensured in each well and plate was left in incubator (37° C., 5% $CO_2$). After 72 hours of incubation an MTT assay was performed and percentage inhibition in proliferation of treated cells was calculated with respect to control cells. Results are given in Table II.

SEQUENCE LISTING OF NEW PEPTIDE ANALOGS

| | | |
|---|---|---|
| DT-11 | Aib-Met-Tyr-Pro-Thr-Tyr-Aib-Lys-OH | (SEQ ID NO: 8) |
| DT-12 | D-Leu-Met-Tyr-Pro-Thr-Tyr-Aib-Lys-OH | (SEQ ID NO: 9) |
| DT-13 | Leu-Met-Tyr-Pro-Thr-D-Tyr-Leu-Lys-OH | (SEQ ID NO: 10) |
| DT-14 | Leu-Met-Tyr-Pro-Thr-Tyr-D-Leu-Lys-OH | (SEQ ID NO: 11) |
| DT-15 | Leu-Met-D-Tyr-Pro-Thr-Tyr-D-Leu-Lys-OH | (SEQ ID NO: 12) |
| DT-16 | D-Leu-Met-Tyr-Pro-Thr-Tyr-D-Leu-Lys-OH | (SEQ ID NO: 13) |
| DT-18 | Aib-Met-Tyr-Pro-Thr-Tyr-Deg-Lys-OH | (SEQ ID NO: 14) |
| DT-19 | D-Leu-Met-Tyr-Pro-Thr-Tyr-Deg-Lys-OH | (SEQ ID NO: 15) |
| DT-23 | D-Phe-Gln-Trp-Aib-Val-Gly-His-Leu-$NH_2$ | (SEQ ID NO: 16) |
| DT-24 | D-Phe-Gln-Trp-Ala-Val-Aib-His-Leu-$NH_2$ | (SEQ ID NO: 17) |
| DT-26 | D-Phe-Gln-Trp-Aib-Val-Gly-His-Ile-$NH_2$ | (SEQ ID NO: 18) |
| DT-27 | D-Phe-Gln-Trp-Ala-Val-Aib-His-Ile-$NH_2$ | (SEQ ID NO: 19) |
| DT-31 | Aib-Met-Gln-Trp-Phe-Aib-$NH_2$ | (SEQ ID NO: 20) |
| DT-33 | D-Leu-Met-Gln-Trp-Phe-Aib-$NH_2$ | (SEQ ID NO: 21) |
| DT-34 | D-Arg-Pro-Lys-Aib-Gln-D-Trp-Phe-D-Trp-Aib-Leu-$NH_2$ | (SEQ ID NO: 22) |
| DT-62A | Ala-Aib-Cys-Lys-Asn-Phe-Phe-D-Trp-Lys-Thr-Phe-Thr-Ser-Cys (3–14 Disulphide bond) | (SEQ ID NO: 23) |
| DT-62B | Ala-Aib-Cys-Lys-Asn-Phe-Phe-D-Trp-Lys-Thr-Phe-Thr-Ser-Cys | (SEQ ID NO: 24) |
| DT-71 | D-Phe-Cys-Tyr-D-Trp-Lys-Thr-Aib-Thr-$NH_2$ | (SEQ ID NO: 25) |

TABLE 2

| | PERCENT INHIBITION OF PROLIFERATION | | |
|---|---|---|---|
| COMPOUND | $10^{-7}$M | $10^{-8}$M | $10^{-9}$M |
| DT-11 | 16.7 | 18.7 | 19.9 |
| DT-12 | 20.3 | 16.1 | 15.5 |
| DT-13 | 22.6 | 20.3 | 18.4 |
| DT-14 | 17.0 | 6.0 | 20.5 |
| DT-15 | 20.4 | 13.2 | 20.0 |
| DT-16 | 24.0 | 24.7 | 37.9 |
| DT-18 | 23.3 | 10.9 | 14.4 |
| DT-19 | 11.9 | 7.3 | 21.0 |
| DT-23 | 3.5 | 17.2 | 30.0 |
| DT-24 | 6.4 | 9.8 | 10.7 |
| DT-26 | 0 | 0 | 0 |
| DT-27 | 14.3 | 11.9 | 6.7 |
| DT-31 | 1.3 | 14.1 | 6.1 |
| DT-33 | 8.7 | 15.8 | 13.9 |
| DT-34 | 12.1 | 15.6 | 14.3 |
| DT-62A | 11.7 | 20.1 | 25.7 |
| DT-62B | 14.0 | 3.8 | 12.8 |
| | $10.^{-8}$M | $10^{-9}$M | $10^{-10}$M |
| DT-71 | 14.6 | 12.1 | 9.4 |

EXAMPLE 3

Polycarbonate filter transwell inserts (24 well size) with 8 μm pores (Nunc, Denmark) were used for the migration assay. ECV304 ($10^4$ cells/200 ul DMEM containing 0.1% BSA) was added to the upper chamber. The lower chamber contained 600 ul of DMEM with 0.1% BSA. Individual peptides of the composition MuJ-7 at six different concentrations each of N/100, N/10, N, 10N, 100N and 1000N were added directly to the upper well and the plate incubated at 37° C. for 24 hours. The cells migrated to the lower chamber were viewed randomly at five different phase-contrast microscopic fields and the total number of cells counted using Video Pro 32 Image Analysis system. Percent inhibition in migration was determined with reference to the Control. Similarly, five different concentrations of N/100, N/10, N, 10N, 100N and 1000N of MuJ-7 were added directly to the upper well and the plate incubated at 37° C. for 24 hours. The cells migrated to the lower chamber were counted as described above. The molarity representing N for each peptide is given in Table No. 3.

TABLE 3

Percent inhibition in migration of endothelial cells ECV.304 across a 8μ filter on treatment with various concentrations of MuJ-7 and its constituent peptides.

| | Percent inhibition in migration (%) | | | | | |
|---|---|---|---|---|---|---|
| Peptide | N/100 | N/10 | N | 10N | 100N | 1000N |
| $VIP_2$ | 0.00 | 91.75 | 89.05 | 88.15 | 92.90 | 0.00 |
| $BOM_1$ | 0.00 | 18.25 | 32.85 | 24.10 | 63.95 | 0.00 |
| $SP_1$ | 13.97 | 94.10 | 90.50 | 92.65 | 78.10 | 18.10 |

TABLE 3-continued

Percent inhibition in migration of endothelial cells ECV.304 across a 8μ filter on treatment with various concentrations of MuJ-7 and its constituent peptides.

Percent inhibition in migration (%)

| Peptide | N/100 | N/10 | N | 10N | 100N | 1000N |
|---|---|---|---|---|---|---|
| VIP$_1$ | 37.53 | 52.60 | 69.40 | 62.60 | 66.52 | 0.00 |
| VIP$_3$ | 0.00 | 32.80 | 92.45 | 23.90 | 11.62 | 0.00 |
| SOM$_2$ | 7.21 | 90.70 | 92.30 | 89.75 | 82.15 | 58.00 |
| SOM$_1$ | 84.27 | 78.50 | 88.11 | 88.75 | 73.73 | 25.00 |
| MuJ-7 | 0.00 | 93.39 | 95.69 | 97.30 | 21.6 | — | where the value of N for each peptide is $10^{-8}$ M for VIP$_2$, BOM$_1$, SP$_1$, VIP$_3$, and SOM$_2$ and $10^{-7}$M for VIP$_1$, and $10^{-9}$M for SOM$_1$.

EXAMPLE 4

Polycarbonate filter trasnwell inserts (24 well size) with 8 μm pores (Nuno, Denmark) were used for the migration assay. ECV304 ($10^4$ cells/200 ul DMEM containing 0.1% BSA) was added to the upper chamber. The lower chamber contained 600 ul of DMEM with 0.1% BSA. Individual peptides at optimum concentration (as indicated in Table 4) were added directly to the upper well and the plate incubatedat 37° C. for 24 hours. The sequence of each of the peptides added are described above. The cells migrated to the lower chamber were viewed randomly at five different phase-contrast microscopic fields and the total number of cells counted using Video Pro 32 Image Analysis system. Percent inhibition in migration was determined with reference to Control.

TABLE 4

Percent inhibition in migration of endothelial cells ECV304 across a 8μ filter on treatment with analogs

| COMPOUND | PERCENT INHIBITION MIGRATION |
|---|---|
| DT-11(-8M) | 82.5 |
| DT-12 (-8M) | 58.7 |
| DT-13 (-8M) | 89.7 |
| DT-14 (-8M) | 77.3 |
| DT-15 (-8M) | 73.2 |
| DT-16 (-8M) | 90.07 |
| DT-18 (-8M) | 73.2 |
| DT-19 (-8M) | 80.4 |
| DT-23 (-8M) | 0 |
| DT-24 (-8M) | 0 |
| DT-26 (-8M) | 0 |
| DT-27 (-8M) | 0 |
| DT-31 (-8M) | 0 |
| DT-33 (-8M) | 41.4 |
| DT-34 (-8M) | 53.6 |
| DT-62A (-8M) | 62.2 |
| DT-62B (-8M) | 8.5 |
| DT-71 (-9M) | 68.2 |

EXAMPLE 5

Polycarbonate filter transwell inserts (24 well size) with 8 μm pores (Nunc, Denmark) were used for the migration assay as described in the previous example. ECV304 ($10^4$ cells/200 ul DMEM containing 0.1% BSA) was added to the upper chamber. The lower chamber contained 600 ul of DMEM with 0.1% BSA. Ten different subcombinations of MuJ-7 listed in Table 5 were tested for inhibition of migration of endothelial cells across the filter as described previously. None of the ten subcombinations caused percent inhibition of migration greater than MuJ-7 and was in the range of 11.3 to 69.3% (Table 6).

TABLE 5

Ten combinations of MuJ-7 with different ratios of its constituent peptides.

| Combination | VIP$_1$ | VIP$_2$ | VIP$_3$ | SOM$_1$ | SOM$_2$ | BOM$_1$ | SP$_1$ |
|---|---|---|---|---|---|---|---|
| MuJ-7 | -7 | -8 | -8 | -9 | -8 | -8 | -8 |
| 1 | -8 | -8 | -8 | -9 | -8 | -8 | -6 |
| 2 | -6 | -8 | -8 | -9 | -8 | -8 | -10 |
| 3 | -7 | -9 | -8 | -9 | -8 | -6 | -8 |
| 4 | -7 | -7 | -8 | -9 | -8 | -10 | -8 |
| 5 | -7 | -6 | -7 | -9 | -8 | -8 | -8 |
| 6 | -7 | -10 | -9 | -9 | -8 | -8 | -8 |
| 7 | -5 | -8 | -8 | -9 | -8 | -8 | -7 |
| 8 | -9 | -8 | -8 | -9 | -8 | -8 | -9 |
| 9 | -7 | -8 | -6 | -9 | -8 | -7 | -8 |
| 10 | -7 | -8 | -10 | -9 | -8 | -9 | -8 |

TABLE 6

Percent inhibition in migration of endothelial cells ECV.304 across a 8μ filter on treatment with ten different combinations of MuJ-7

| Subcombination | % Inhibition Migration |
|---|---|
| MuJ-7 | 95.7 |
| 1 | 38.6 |
| 2 | 69.3 |
| 3 | 19.3 |
| 4 | 50.0 |
| 5 | 11.3 |
| 6 | 28.4 |
| 7 | 13.6 |
| 8 | 37.5 |
| 9 | 32.9 |
| 10 | 25.0 |

EXAMPLE 6

Matrigel (350 ul) was placed into each well of a 24-well culture plate at 4° C. and was allowed to polymerize by incubation at 37° C. for 30 min. ECV304 (1.5×$10^4$) were seeded on the Matrigel in 500 ul DMEM supplemented with 10% FBS. MuJ-7 at four different concentrations of 0.25×, 0.5×, ×, & 5.0× were added and. the plate incubated at 37° C. for 24 hour. "×" denotes normal concentration of MuJ-7 where molar concentration of individual peptides was $10^{-8}$ M for VIP$_2$, BOM$_1$, SP$_1$, VIP$_3$ and SOM$_2$ and $10^{-7}$ M for VIP$_1$ and $10^{-9}$ M for SOM$_1$. Tube like structures formed, the area of which was individually counted at five different phase-contrast microscopic fields using Video Pro 32 Image Analysis system. Percent inhibition in tube area was determined with reference to untreated cells.

TABLE 7

Percent inhibition in Tube-like-structure (TLS) area on treatment with various concentrations of MuJ-7.

| Concentration of MuJ-7 | Percent in tube area |
| --- | --- |
| 0.25x | 28.4 |
| 0.5x | 39.3 |
| x | 47.8 |
| 5.0x | 58.1 |

EXAMPLE 7

Matrigel (350 ul) was placed into each well of a 24-well culture plate at 4° C. and was allowed to polymerize by incubation at 37° C. for 30 min. ECV304 ($1.5 \times 10^4$) were seeded on the Matrigel in 500 ul DMEM supplemented with 10% FBS. New analogs of peptides as shown in FIG. 1 were added at optimum concentration as denoted in Table 8, and the plate incubated at 37° C. for 24 hours. Tube like structures formed, the area of which was individually counted at five different phase-contrast microscopic fields using Video Pro 32 Image Analysis system. Percent inhibition in tube length was determined with reference to untreated cells.

TABLE 8

| PEPTIDE | SPROUTING | INTUSSUSCEPTION | TUBE FORMATION | INHIBITION OF TUBE LENGTH |
| --- | --- | --- | --- | --- |
| DT-10 (-8M) | + | + | + | 59.5 |
| DT-11 (-8M) | ++ | + | + | 3.6 |
| DT-12 (-8M) | ++ | + | ++ | 17.1 |
| DT-13 (-8M) | ++ | ++ | ++ | 16.2 |
| DT-14 (-8M) | ++ | + | + | 24.3 |
| DT-15 (-8M) | ++ | + | ++ | 0 |
| DT-16 (-8M) | ++ | + | + | 18.9 |
| DT-18 (-8M) | ++ | ++ | ++ | 0 |
| DT-19 (-8M) | ++ | + | + | 37.8 |
| DT-23 (-8M) | + | + | + | 53.1 |
| DT-24 (-8M) | ++ | + | + | 16.2 |
| DT-26 (-8M) | ++ | ++ | ++ | 0 |
| DT-27 (-8M) | + | + | + | 29.7 |
| DT-31 (-8M) | + | + | + | 17.1 |
| DT-33 (-8M) | ++ | ++ | ++ | 13.5 |
| DT-34 (-8M) | ++ | ++ | ++ | 0 |
| DT-62A (-8M) | ++ | + | ++ | 44.1 |
| DT-62B (-8M) | ++ | ++ | ++ | 0 |
| DT-71 (-9M) | ++ | + | ++ | 9.9 | although sprouting was visible at day 1, intussusception was still missing. However, endothelial cells treated PTC culture supernatant showed enhanced sprouting as well as intussusception leading to completion of tube formation. This clearly suggests pro-angiogenic activity of factors in culture supernatant of primary tumor cells of human colon adenocarcinoma. Treating PTC culture supernatant treated endothelial cells with MuJ-7 resulted in complete inhibition of intussusception and a significant decrease in sprouting. This indicates the ability of MuJ-7 to inhibit two key steps of a new blood vessel formation, i. e., sprouting and angiogenesis. A qualitative representation of the effect is given in Table 9.

TABLE 9

Qualitative representation of the effect of MuJ-7 on Tube-like-structure activity of PTC culture supernatant stimulated endothelial cells.

| | Untreated | PTC culture supernatant stimulated | MuJ-7 treated |
| --- | --- | --- | --- |
| Sprouting | ++ | +++ | + |
| Intussusception | + | ++ | − |
| Tube formation | + | ++ | − |

EXAMPLE 8

Matrigel (350 ul) was placed into each well of a 24-well culture plate at 4° C. and was allowed to polymerize by incubation at 37° C. for 30 min. ECV304 ($1.5 \times 10^4$) were seeded on the Matrigel in each of the 24 wells. 500 ul DMEM supplemented with 10% FBS and was added to 8 wells. These wells served as controls. Culture supernatants of primary tumor cells of human colon adenocacinoma from a confluent culture in log phase of growth was filtered through a 0.22 u filter and its pH adjusted to 7.4 with sodium bicarbonate. 500 ul of this supernatant was added to another 8 wells, containing ECV304 ($1.5 \times 10^4$) cells seeded on Matrigel. To the remaining 8 wells, MuJ-7 was added and incubated at 37° C. for 24 hours. Five different phase-contrast microscopic fields (4x) were reviewed and total tube length of the tube-like-structures (TLS) measured using Video Pro 32 Image Analysis system. Percent inhibition of TLS was calculated with reference to Controls. In controls,

EXAMPLE 9

Matrigel (350 ul) was placed into each well of a 24-well culture plate at 4° C. and was allowed to polymerize by incubation at 37° C. for 30 min. ECV304 ($1.5 \times 10^4$) were seeded on the Matrigel in 500 ul DMEM supplemented with 10% FBS. Individual peptides of the composition MuJ-7 at three different concentrations each of N/10, N, and 10N were added and the plate incubated at 37° C. for 24 hours. Tube like structures formed, the length of which were individually counted at five different phase-contrast microscopic fields using Video Pro 32 Image Analysis system. Percent inhibition in tube length was determined with reference to Control. Similarly, three different concentrations of N/10, N, and 10N of MuJ-7 were added to the well and the plate incubated at 37° C. for 24 hours. Percent inhibition in tube length was determined with reference to Control as described previously (Table 10).

TABLE 10

Percent inhibition in Tube-like-structure (TLS) length on treatment with various concentrations of MuJ-7 and its constituent peptides.

| Peptide | Percent inhibition in TLS activity (%) | | |
|---|---|---|---|
| | N/10 | N | 10N |
| $VIP_2$ | 0.0 | 1.0 | 3.3 |
| $BOM_1$ | 0.0 | 0.0 | 2.9 |
| $SP_1$ | 14.4 | 8.9 | 3.0 |
| $VIP_1$ | 14.9 | 11.7 | 13.1 |
| $VIP_1$ | 8.5 | 22.1 | 17.9 |
| $SOM_2$ | 1.0 | 16.5 | 16.8 |
| $SOM_2$ | 7.0 | 15.1 | 16.7 |
| MuJ-7 | 6.9 | 15.6 | 22.27 | where the value of N for each peptide is $10^{-8}M$ for $VIP_2$, $BOM_1$, $SP_1$, $VIP_3$, and $SOM_2$ and $10^{-7}M$ for $VIP_1$, and $10^{-9}M$ for $SOM_1$.

EXAMPLE 10

Matrigel (350 ul) was placed into each well of a 24-well culture plate at 4° C. and was allowed to polymerize by incubation at 37° C. for 30 min. ECV304 ($1.5 \times 10^4$) were seeded on the Matrigel in each of the 24 wells. 500 ul DMEM supplemented with 10% FBS was added to 8 wells. These wells served as controls. Culture supenatants of primary tumor cells of human colon adenocarcinoma from a confluent culture in log phase of growth was filtered through a 0.22 u filter and its pH adjusted to 7.4 with sodium bicarbonate. 500 ul of this supernatant was added to another 8 wells contains ECV304 ($1.5 \times 10^4$) cells seeded on Matrigel. To the remains 8 wells, MuJ-7 was added and incubated at 37° C. for 24 hours. Five different phase-contrast microscopic fields (4x) were viewed and total tube length of the tube-like-structures (TLS) measured using Video Pro 32 Image Analysis system. Percent inhibition of TLS was calculated with reference to Controls. In controls, 76.9% of TLS were in the range of 50–69 μm and remaining were between 69–107 μm. There were no structures greater than 107 μm. In PTC stimulated wells, the percentage of TLS in range of 50–69 μm reduced to 50.0% while 27.3% were in the range of 69–107 μm. It is interesting to note that there were approximately 18.0% TLS in the range of 107–183 μm and 4.55% TLS in 221–240 μm. Hence there was a significant increase in the length of TLS in PTC supernatant stimulated cells as compared to the unstimulated controls. This clearly suggests pro-angiogenic activity of factors in culture supernatant of primary tumor cells of human colon adenocarcinoma. In the third group of wells, which were treated with MuJ-7, 81.25% TLS were in the range of 50–69 μm and 18.75% in the range of 69–88 μm (Table 6). This reversal of TLS activity to control level on treatment with MuJ-7 clearly suggests anti angiogenic activity of MuJ-7.

TABLE 11

Percent inhibition in TLS length of PTC culture supernatant endothelial cells treated with MuJ-7.

| Tube length Range (in microns) | Controls | PTC culture supernatant stimulated | MuJ-7 treated |
|---|---|---|---|
| 50–69 | 76.92 | 50.00 | 81.25 |
| 69–88 | 7.69 | 4.55 | 18.75 |
| 88–107 | 15.38 | 22.73 | 0.00 |
| 107–126 | 0.00 | 4.55 | 0.00 |
| 126–145 | 0.00 | 9.09 | 0.00 |
| 145–164 | 0.00 | 0.00 | 0.00 |
| 164–183 | 0.00 | 4.55 | 0.00 |
| 183–202 | 0.00 | 0.00 | 0.00 |
| 202–221 | 0.00 | 0.00 | 0.00 |
| 221–240 | 0.00 | 4.55 | 0.00 |

REFERENCES

1. Cancer: Principles & Practice of Oncology, Fifth Edition, edited by Vincent T. DeVita, Jr., Samuel Hellinan, Steven A. Rosenberg. Lippincott-Raven Publishers, Philadelphia © 1997.
2. Hanahan, D. Signalling vascular morphogenesis and maintenance. Science 277, 48–50(1997).
3. Risau, W. Mechanisms of angiogenesis. Nature 386, 671–674 (1997).
4. Folkman, J. Tumor angiogenesis. in The Molecular Basis of Cancer (eds. Mendelsohn, J., Howley, P. M., Israel, M. A., & Liotta, L. A.) 206–232 (W. B. Saunders, Philadelphia, 1995).
5. Patan, S., Munn, L. L. & Jain, R. K. Intussusceptive microvascular growth in a human colon adenocarcinoma xenograft: A novel mechanism of tumaor angiogenesis. Microvasc. Res. 51, 260–272 (1996).
6. Jain, R. K., Schlenger, K., Hockel, M., Yuan, F., Quantitative angiogenesis assays: Progress and problems. Nature medicine, 3(11), 1203–08, (1997).
7. Folkman, J. Tumor angiogenesis: Therapeutic implications. N. Engl. J. Med., 285, 1182 (1971).
8. Folkman, J. Auti-angiogenesis: new concept for therapy for therapy of solid tumors. Ann Surg., 175, 148, (1972).
9. Hanahan D, Folkman, J. Patterns and emerging mechanisms for the angiogenic switch during tumorigenesis. Cell, 86, 353, (1996).
10. O'Reilly, M S, Holmgren L, Shing Y, Chen C, Rosenthal R A, Moses M, Lane W S, Cao Y, Sage E H, Folkm N J. Arigiostatin: a novel angiogenesis inhibitor that mediates the suppression of metastases by a Lewis lung carcinoma. Cell, 19, 315 (1994).
11. O'Reilly, M S, Holmgren L, Chen C, Folkman J. Angiostatin induces and sustains dormancy of human primary tumors in mice. Nature Med, 2, 689 (1996).
12. Folkman, J. Tumor angiogenesis. In: Holland J R, Frei E, Bast R, Kule D, Morton D, Weichselbaum R, eds. Cancer medicine, ed 4. Baltimore: Williams & Wilkins (1996).
13. Modzelewski R A, Davies P, Watkins S C, Auerbach R, Chang M-J, Johnson C S. Isolation and identification of fresh tumor-derived endothelial cells from a murine RIF-1 fibrosarcoma. Cancer Res 54, 336 (1994).
14 Holmgren L, O'Reilly, M S, Folkman J. Dormancy of micrometastases: balanced proliferation and apoptosis in the presence of angiogenesis suppression. Nature Med 1, 149 (1995).
15. Teicher B A, Holden S A, Gulshan A, Alvarez Sotoinayer E, Huang S D, Chen Y-N, Brem H. Potentiation of cytotoxic cancer therapies by TNP-470 alone and with other antiangiogenic agents. Int J Cancer 57,920 (1994).

16. Dawson D W, Pearse S F, Zhong R, Silverstein R L, Frazier W A, Bouck N P CD36 mediates the Invitro inhibitory effects of thrombospondin-1 on endothelial cells. J Cell Bio; 138(3): 707–17 (1997).
17. Anand-Apte B, Bao L, Smith R, Iwata K, Olsen B R Zetter B, Apte S S.
A review of tissue inhibitor of metalloproteinases-3 (TIMP-3) and experimental analysis of its effect on primary tumor growth. Biochem Cell Biol; 74(6): 853–62 (1996).
18. Yeung, A K. Human cytostatin, a novel anti-angiogenic cytokine. Diss Abstr Int(B); 55(12): 5300 (1995).
19. Wu Z, O'Reilly M S, Folkman J, Shing Y. Suppression of tumor growth with recombinant murine angiostatin. Biochem Biophys Res Commun; 236(3); 651–4 (1997).
20. Minchinton A I, Fryer K H, Wendt K R, Clow K A, Hayes M M. The effect of thalidomide on experimental tumors and metastases.
Anticancer Drugs: 7(3): 339–43 (1996).
21. Dameso R, Del Tacca M. The effects of the somatostatin analog octreotide on angiogenesis in vitro. Metabolism 45(8): 49–50 (1996).
22. Woltering E A, Barrie R, O'Dorisio T M, Arce D, Ure T, Cramer A, Holmes D, Robertson J, Fassler J. Somatostatin analogues inhibit angiogenesis in the chick chorioallantoic membrane. J Surg Res 50(3): 245–251 (1991).
23. Wiedermann C J, Auer B, Sitte B, Reinisch N, Schratzberger P, Kahler C M Induction of endothelial cell differentiation into capillary-like structures by substance P. Eur J Pharmacol 298(3): 335–338 (1996).
24. Ziche M, Morbidelli L, Masini E, Amerini S, Granger H J, Maggi C A, Geppetti P, Ledda F. Nitric oxide mediates angiogenesis in vivo and endothelial cell growth and migration in vitro promoted by substance P. J Clin Invest 94(5): 2036–2044 (1994).
25. Hu D E, Hiley C R, Fan T P. Comparative studies of the angiogenie activity of vasoactive intestinal peptide, endothelins-1 and -3 and angiotensin II in a rat sponge model. Br J Pharmacol 117(3): 545–551 (1996).

What is claimed is:

1. An isolated peptide selected from the group consisting of:

| | |
|---|---|
| Aib-Met-Tyr-Pro-Thr-Tyr-Aib-Lys-OH | (SEQ ID NO: 8) |
| D-Leu-Met-Tyr-Pro-Thr-Tyr-Aib-Lys-OH | (SEQ ID NO: 9) |
| Leu-Met-Tyr-Pro-Thr-D-Tyr-Leu-Lys-OH | (SEQ ID NO: 10) |
| Leu-Met-Tyr-Pro-Thr-Tyr-D-Leu-Lys-OH | (SEQ ID NO: 11) |
| Leu-Met-D-Tyr-Pro-Thr-Tyr-D-Leu-Lys-OH | (SEQ ID NO: 12) |
| D-Leu-Met-Tyr-Pro-Thr-Tyr-D-Leu-Lys-OH | (SEQ ID NO: 13) |
| Aib-Met-Tyr-Pro-Thr-Tyr-Deg-Lys-OH | (SEQ ID NO: 14) |
| D-Leu-Met-Tyr-Pro-Thr-Tyr-Deg-Lys-OH | (SEQ ID NO: 15) |
| D-Phe-Gln-Trp-Aib-Val-Gly-His-Leu-NH$_2$ | (SEQ ID NO: 16) |
| D-Phe-Gln-Trp-Ala-Val-Aib-His-Leu-NH$_2$ | (SEQ ID NO: 17) |
| D-Phe-Gln-Trp-Aib-Val-Gly-His-Ile-NH$_2$ | (SEQ ID NO: 18) |
| D-Phe-Gln-Trp-Ala-Val-Aib-His-Ile-NH$_2$ | (SEQ ID NO: 19) |
| Aib-Met-Gln-Trp-Phe-Aib-NH$_2$ | (SEQ ID NO: 20) |
| D-Leu-Met-Gln-Trp-Phe-Aib-NH$_2$ | (SEQ ID NO: 21) |
| D-Arg-Pro-Lys-Pro-Aib-Gln-D-Trp-Phe-D-Trp-Aib-Leu-NH$_2$ | (SEQ ID NO: 22) |
| Ala-Aib-Cys-Lys-Asn-Phe-Phe-D-Trp-Lys-Thr-Phe-Thr-Ser-Cys (3–14 Disulphide bond) | (SEQ ID NO: 23) |
| Ala-Aib-Cys-Lys-Asn-Phe-Phe-D-Trp-Lys-Thr-Phe-Thr-Ser-Cys and | (SEQ ID NO: 24) |
| D-Phe-Cys-Tyr-D-Trp-Lys-Thr-Aib-Thr-NH$_2$ | (SEQ ID NO: 25) | wherein Aib=α-Aminoisobutyric acid, Deg=α, Diethyl glycine.

2. A composition comprising a peptide set forth in claim 1 and a physiologically acceptable carrier, diluent or solvent.

3. A composition comprising a combination of a peptide of the amino acid sequence Ala-Gly-Cys-Lys-Asn-Phe-Phe-D-Trp-Lys-Thr-Phe-Thr-Ser-D-Cys (SEQ ID NO:5) having a disulfide bridge between Cys and Ser (SOM$_2$), and at least four peptides selected from the group consisting of VIP$_1$, VIP$_2$, VIP$_3$, SOM$_1$, BOM$_1$ and SP$_1$ wherein VIP$_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-NH$_2$ (SEQ ID NO:1) VIP$_2$is of the amino acid sequence Leu-Met-Tyr-Pro-Thr-Tyr-Leu-Lys (SEQ ID NO: 2), VIP$_3$ is of the amino acid sequence His-Ser-Asp-Ala-Val4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:3), SOM$_1$ is of the amino acid sequence D-Phe-Cys-Tyr-D-Trp-Orn-Thr-Pen-Thr-NH$_2$ (SEQ ID NO:4), BOM$_1$ is of the amino acid sequence D-Phe-Gln-Trp-Ala-Val-Gly-His-Leu-NHEt (SEQ ID NO:6) and SP$_1$ is of the amino acid sequence D-Arg-Pro-Lys-Pro-D-Phe-Gln-D-Trp-Phe-D-Trp-Leu-Leu-NH$_2$ (SEQ ID NO: 7), the combination comprising an amount of each peptide wherein the combination is effective to inhibit the proliferation of tumor or cancer cells.

4. A composition as claimed in claim 3, wherein the concentration of VIP$_1$ is about 10$^{-7}$M, the concentration of VIP$_2$ is about 10$^{-8}$M, the concentration of VIP$_3$ is about 10$^{-8}$M, the concentration of SOM$_1$ is about 10$^{-9}$M, the concentration of SOM$_2$ is about 10$^{-7}$M, the concentration of BOM$_1$ is about 10$^{-8}$M, and the concentration of SP$_1$ is about 10$^{-8}$M.

5. The composition as claimed in claim 3, wherein the molar ratio of VIP$_1$:VIP$_2$: VIP$_3$: SOM$_1$:SOM$_2$:BOM$_1$:SP$_1$ is about 1.0:0.1:0.1:0.01:0.1:0.1:0.1.

6. The composition as claimed in claim 3, further comprising a physiologically acceptable carrier, diluent or solvent.

7. The composition as claimed in claim 3, wherein the composition comprises a combination of VIP$_1$, VIP$_2$, SOM$_1$, SOM$_2$ and BOM$_1$ wherein the combination comprises an amount of each peptide wherein the combination is effective to inhibit the proliferation of tumor or cancer cells.

8. The composition as claimed in claim 3 wherein the composition comprises a combination of VIP$_1$, VIP$_2$, VIP$_3$, SOM$_1$, SOM$_2$ and SP$_1$ wherein the combination comprises an amount of each peptide wherein the combination is effective to inhibit the proliferation of tumor or cancer cells.

9. A composition comprising a combination of a peptide of the amino acid sequence Ala-Gly-Cys-Lys-Asn-Phe-Phe-D-Trp-Lys-Thr-Phe-Thr-Ser-D-Cys (SEQ ID NO:5) having a disulfide bridge between Cys and Ser (SOM$_2$), and at least four peptides selected from the group consisting of VIP$_1$, VIP$_2$, VIP3, SOM$_1$, BOM$_1$ and SP$_1$ wherein VIP$_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-NH$_2$ (SEQ ID NO:l) VIP$_2$is of the amino acid sequence Leu-Met-Tyr-Pro-Thr-Tyr-Leu-Lys (SEQ ID NO: 2), VIP$_3$ is of the amino acid sequence His-Ser-Asp-Ala-Val4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ SEQ ID NO:3), SOM$_1$ is of the amino acid sequence D-Phe-Cys-Tyr-D-Trp-Orn-Thr-Pen-Thr-NH$_2$ (SEQ ID NO:4), BOM$_1$ is of the amino acid sequence D-Phe-Gln-Trp-Ala-Val-Gly-His-Leu-NHEt (SEQ ID NO:6) and SP$_1$ is of the amino acid sequence D-Arg-Pro-Lys-Pro-D-Phe-Gln-D-Trp-Phe-D-Trp-Leu-Leu-NH$_2$ (SEQ ID NO: 7), the combination comprising an amount of each peptide wherein the combination is effective to inhibit the proliferation of endothelial cells.

10. A composition comprising a combination of a peptide of the amino acid sequence Ala-Gly-Cys-Lys-Asn-Phe-Phe-D-Trp-Lys-Thr-Phe-Thr-Ser-D-Cys (SEQ ID NO:5) having a disulfide bridge between,Cys and Ser (SOM$_2$), and at least four peptides selected from the group consisting of VIP$_1$, VP$_2$, VIP$_3$, SOM$_1$, BOM$_1$ and SP$_1$ wherein VIP$_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-NH$_2$ (SEQ ID NO:1) VIP$_2$is of the amino acid sequence Leu-Met-Tyr-Pro-Thr-Tyr-Leu-Lys (SEQ ID NO: 2), VIP$_3$ is of the amino acid sequence His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:3), SOM$_1$ is of the amino acid sequence D-Phe-Cys-Tyr-D-Trp-Orn-Thr-Pen-Thr-NH$_2$ (SEQ ID NO:4), BOM$_1$ is of the amino acid sequence D-Phe-Gln-Trp-Ala-Val-Gly-His-Leu-NHEt (SEQ ID NO:6) and SP$_1$ is of the amino acid sequence D-Arg-Pro-Lys-Pro-D-Phe-Gln-D-Trp-Phe-D-Trp-Leu-Leu-NH$_2$ (SEQ ID NO: 7), the combination comprising an amount of each peptide wherein the combination is effective to inhibit the migration of tumor or cancer cells.

11. A composition comprising a combination of a peptide of the amino acid sequence Ala-Gly-Cys-Lys-Asn-Phe-Phe-D-Trp-Lys-Thr-Phe-Thr-Ser-D-Cys (SEQ ID NO:5) having a disulfide bridge between Cys and Ser (SOM$_2$), and at least four peptides selected from the group consisting of VIP$_1$, VIP$_2$, VIP$_3$, SOM$_1$, BOM$_1$ and SP$_1$ wherein VIP$_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-NH$_2$ (SEQ ID NO:1) VIP$_2$is of the amino acid sequence Leu-Met-Tyr-Pro-Thr-Tyr-Leu-Lys (SEQ ID NO: 2), VIP$_3$ is of the amino acid sequence His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO:3), SOM$_1$ is of the amino acid sequence D-Phe-Cys-Tyr-D-Trp-Orn-Thr-Pen-Thr-NH$_2$ (SEQ ID NO:4), BOM$_1$ is of the amino acid sequence D-Phe-Gln-Trp-Ala-Val-Gly-His-Leu-NHEt (SEQ ID NO:6) and SP$_1$ is of the amino acid sequence D-Arg-Pro-Lys-Pro-D-Phe-Gln-D-Trp-Phe-D-Trp-Leu-Leu-NH$_2$ (SEQ ID NO: 7), the combination comprising an amount of each peptide wherein the combination is effective to inhibit the growth of tubes from tumor or cancer cells.

12. A method for inhibiting the proliferation of tumor or cancer cells which comprises contacting the tumor or cancer cells in vitro with an amount of a composition comprising SOM$_2$ of the amino acid sequence Ala-Gly-Cys-Lys-Asn-Phe-Phe-D-Tr-Lys-Thr-Phe-Thr-Ser-D-Cys (SEQ ID NO:5) having a disulfide bridge between Cys and Ser and at least four peptides selected from the group consisting of VIP$_1$, VIP$_2$, VIP$_3$, SOM$_1$, BOM$_1$ and SP$_1$ wherein VIP$_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-NH$_2$ (SEQ ID NO: 1), VIP$_2$ is of the amino acid sequence Leu-Met-Tyr-Pro-Thr-Tyr-Leu-Lys (SEQ ID NO: 2), VIP$_3$ is of the amino acid sequence His-Ser-Asp-Ala-Val4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-NH$_2$ (SEQ ID NO: 3), SOM$_1$ is of the amino acid sequence D-Phe-Cys-Tyr-D-Trp-Orn-Thr-Pen-Thr-NH$_2$ (SEQ ID NO: 4), BOM, is of the amino acid sequence D-Phe-Gln-Trp-Ala-Val-Gly-His-Leu-NHEt (SEQ ID NO: 6) and SP$_1$ is of the amino acid sequence D-Arg-Pro-Lys-Pro-D-Phe-Gln-D-Trp-Phe-D-Trp-Leu-Leu-NH$_2$ (SEQ ID NO: 7) effective to inhibit the proliferation of tumor or cancer cells.

13. The method according to claim 12, wherein the composition comprises VIP$_1$, VIP$_2$, VIP$_3$, SOM$_1$, SOM$_2$, BOM$_1$, and SP$_1$.

14. A method according to claim 12, wherein in the composition the concentration of VIP$_1$ is about 10$^{-7}$M, the concentration of VIP$_2$ is about 10$^{-8}$, the concentration of VIP$_3$ is about 10$^{-8}$M, the concentration of SOM$_1$ is about 10$^{-9}$M, the concentration of SOM$_2$ is about 10$^{-7}$M, the concentration of BOM$_1$ is about 10$^{-8}$M, and the concentration of SP$_1$ is about 10$^{-8}$M.

15. The method according to claim 12, wherein the tumor or cancer cells are adenocarcinomas of the colon, breast, lung, prostate, or kidney or leukemia or lymphoma.

16. A method for inhibiting the proliferation of endothelial cells which comprises contacting the endothelial cells in vitro with an amount of a composition comprising $SOM_2$ of the amino acid sequence Ala-Gly-Cys-Lys,Asn-Phe-Phe-D-Trp-Lys-Thr-Phe-Thr-Ser-D-Cys (SEQ ID NO:5) having a disulfide bridge between Cys and Ser and at least four peptides selected from the group consisting of $VIP_1$, $VIP_2$, $VIP_3$, $SOM_1$, $BOM_1$ and $SP_1$ wherein $VIP_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-$NH_2$ (SEQ ID NO: 1), $VIP_2$ is of the amino acid sequence Leu-Met-Tyr-Pro-Thr-Tyr-Leu-Lys (SEQ ID NO: 2), $VIP_3$ is of the amino acid sequence His-Ser-Asp-Ala-Val-4-Cl-D-Phe-Thr-Asp-Asn-Tyr-Thr-Arg-Leu-Arg-Lys-Gln-Leu-Ala,-Val-Lys-Lys-Tyr-Leu-Asn-Ser-Ile-Leu-Asn-$NH_2$ (SEQ ID NO: 3), $SOM_1$ is of the amino acid sequence D-Phe-Cys-Tyr-D-Trp-Orn-Thr-Pen-Thr-$NH_2$ (SEQ ID NO: 4), $BOM_1$ is of the amino acid sequence D-Phe-Gln-Trp-Ala-Val-Gly-His-Leu-NHEt (SEQ ID NO: 6) and $SP_1$ is of the amino acid sequence D-Arg-Pro-Lys-Pro-D-Phe-Gln-D-Trp-Phe-D-Trp-Leu-Leu-$NH_2$ (SEQ ID NO: 7) effective to inhibit the proliferation of endothelial cells.

17. The method according to claim 16, wherein the composition comprises $VIP_1$, $VIP_2$, $VIP_3$, $SOM_1$, $SOM_2$, $BOM_1$, and $SP_1$.

18. A method according to claim 16, wherein in the composition the concentration of $VIP_1$ is about $10^{-7}$M, the concentration of $VIP_2$ is about $10^{-8}$, the concentration of $VIP_3$ is about $10^{-8}$M, the concentration of $SOM_1$ is about $10^{-9}$M, the concentratio of $SOM_2$ is about $10^{-7}$M, the concentration of $BOM_1$ is about $10^{-8}$M, and the concentration of $SP_1$ is about $10^{-8}$M.

19. A method for inhibiting the migration of tumor or cancer cells which comprises contacting the tumor or cancer cells in vitro with an amount of a composition comprising $SOM_2$ of the amino acid sequence Ala-Gly-Cys-Lys-Asn-Phe-Phe-D-Trp-Lys-Thr-Phe-Thr-Ser-D-Cys (SEQ ID NO: 5) having a disulfide bridge between Cys and Ser and at least four peptides selected from the group consisting of $VIP_1$, $VIP_2$, $VIP_3$, $SOM_1$, $BOM_1$ and $SP_1$ wherein $VIP_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-$NH_2$ (SEQ ID NO: 1), $VIP_2$ is of the amino acid sequence Leu-Met-Tyr-Pro-Thr-Tyr-Leu-Lys (SEQ ID NO: 2), $VIP_3$ is of the amino acid sequence His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-$NH_2$ (SEQ ID NO: 3), $SOM_1$ is of the amino acid sequence D-Phe-Cys-Tyr-D-Trp-Orn-Thr-Pen-Thr-$NH_2$ (SEQ ID NO: 4), $BOM_1$ is of the amino acid sequence D-Phe-Gln-Trp-Ala-Val-Gly-His-Leu-NHEt (SEQ ID NO: 6) and $SP_1$ is of the amino acid sequence D-Arg-Pro-Lys-Pro-D-Phe-Gin-D-Trp-Phe-D-Trp-Leu-Leu-$NH_2$ (SEQ ID NO: 7) effective to inhibit the migration of tumor or cancer cells.

20. The method according to claim 19, wherein the composition comprises $VIP_1$, $VIP_2$, $VIP_3$, $SOM_1$, $SOM_2$, $BOM_1$, and $SP_1$.

21. The method according to claim 19, wherein in the composition the concentration of $VIP_1$ is about $10^{-7}$M, the concentration of $VIP_2$ is about $10^{-8}$, the concentration of $VIP_3$ is about $10^{-8}$M, the concentration of $SOM_1$ is about $10^{-9}$M, the concentration of $SOM_2$ is about $10^{-7}$M, the concentration of $BOM_1$ is about $10^{-8}$M, and the concentration of $SP_1$ is about $10^{-8}$M.

22. The method according to claim 19, wherein the tumor or cancer cells are adenocarcinomas of the colon, breast, lung, prostate, or kidney or leukemia or lymphoma.

23. A method for inhibiting the growth of tubes from tumor or cancer cells which comprises contacting the tumor or cancer cells in vitro with an amount of a composition comprising $SOM_2$ of the amino acid sequence Ala-Gly-Cys-Lys-Asn-Phe-Phe-D-Trp-Lys-Thr-Phe-Thr-Ser-D-Cys (SEQ ID NO: 5) having a disulfide bridge between Cys and Ser and at least four peptides selected from the group consisting of $VIP_1$, $VIP_2$, $VIP_3$, $SOM_1$, $BOM_1$ and $SP_1$ wherein $VIP_1$ is of the amino acid sequence Lys-Pro-Arg-Arg-Pro-Tyr-Thr-Asp-Asn-Tyr-Thr-Arg-Leu-Arg-Leu-Arg-Lys-Gln-Met-Ala-Val-Lys-Lys-Tyr-Leu-Asn-Ser-Ile-Leu-Asn-$NH_2$ (SEQ ID NO: 1), $VIP_2$ is of the amino acid sequence Leu-Met-Tyr-Pro-Thr-Tyr-Leu-Lys (SEQ ID NO: 2), $VIP_3$ is of the amino acid sequence His-Ser-Asp-Ala-Val-4-Cl-D-Phe-Thr-Asp-Asn-Tyr-Thr-Arg-Leu-Arg-Lys-Gln-Leu-Ala-Val-Lys-Lys-Tyr-Leu-Asn-Ser-Ile-Leu-Asn-$NH_2$ (SEQ ID NO: 3), $SOM_1$ is of the amino acid, sequence D-Phe-Cys-Tyr-D-Trp-Orn-Thr-Pen-Thr-$NH_2$ (SEQ ID NO: 4), $BOM_1$ is of the amino acid sequence D-Phe-Gln-Trp-Ala-Val-Gly-His-Leu-NHEt (SEQ ID NO: 6) and $SP_1$ is of the amino acid sequence D-Arg-Pro-Lys-Pro-D-Phe-Gln-D-Trp-Phe-D-Trp-Leu-Leu-$NH_2$ (SEQ ID NO: 7) effective to inhibit the growth of tubes from tumor or cancer cells.

24. The method according to claim 23, wherein the composition comprises $VIP_1$, $VIP_2$, VIP3, $SOM_1$, $SOM_2$, $BOM_1$, and $SP_1$.

25. The method according to claim 23, wherein in the composition the concentration of $VIP_1$ is about $10^{-7}$M, the concentration of $VIP_2$ is about $10^{-8}$, the concentration of $VIP_3$ is about $10^{-8}$M, the concentration of $SOM_1$ is about $10^{-9}$M, the concentration of $SOM_2$ is about $10^{-7}$M, the concentration of $BOM_1$ is about $10^{-8}$M, and the concentration of $SP_1$ is about $10^{-8}$M.

26. The method according to claim 23, wherein the tumor or cancer cells are adenocarcinomas of the colon, breast, lung, prostate, or kidney or leukemia or lymphoma.

27. A method for inhibiting the proliferation of tumor or cancer cells comprising contacting the tumor or cancer cells in vitro with an amount of a peptide selected from the group consisting of:

Aib-Met-Tyr-Pro-Thr-Tyr-Aib-Lys-OH (SEQ ID NO: 8)

D-Leu-Met-Tyr-Pro-Thr-Tyr-Aib-Lys-OH (SEQ ID NO: 9)

Leu-Met-Tyr-Pro-Thr-D-Tyr-Leu-Lys-OH (SEQ ID NO: 10)

Leu-Met-Tyr-Pro-Thr-Tyr-D-Leu-Lys-OH (SEQ ID NO: 11)

Leu-Met-D-Tyr-Pro-Thr-Tyr-D-Leu-Lys-OH (SEQ ID NO: 12)

D-Leu-Met-Tyr-Pro-Thr-Tyr-D-Leu-Lys-OH (SEQ ID NO: 13)

Aib-Met-Tyr-Pro-Thr-Tyr-Deg-Lys-OH (SEQ ID NO: 14)

D-Leu-Met-Tyr-Pro-Thr-Tyr-Deg-Lys-OH (SEQ ID NO: 15)

D-Phe-Gln-Trp-Aib-Val-Gly-His-Leu-$NH_2$ (SEQ ID NO: 16)

D-Phe-Gln-Trp-Ala-Val-Aib-His-Leu-$NH_2$ (SEQ ID NO: 17)

D-Phe-Gln-Trp-Aib-Val-Gly-His-Ile-$NH_2$ (SEQ ID NO: 18)

D-Phe-Gln-Trp-Ala-Val-Aib-His-Ile-NH2 (SEQ ID NO: 19)

Aib-Met-Gln-Trp-Phe-Aib-$NH_2$ (SEQ ID NO: 20)

D-Leu-Met-Gln-Trp-Phe-Aib-$NH_2$ (SEQ ID NO: 21)

D-Arg-Pro-Lys-Aib-Gln-D-Trp-Aib-Leu-$NH_2$ (SEQ ID NO: 22)

Ala-Aib-Cys-Lys-Asn-Phe-Phe-D-Trp-Lys-Thr-Phe-Thr-Ser-Cys (3-14 Disulphide Bond) (SEQ ID NO: 23)

Ala-Aib-Cys-Lys-Asn-Phe-Phe-D-Trp Lys-Thr-Phe-Thr-Ser-Cys (SEQ ID NO: 24) and

D-Phe-Cys-Tyr-D-Trp-Lys-Thr-Aib-Thr-NH$_2$ (SEQ ID NO: 25)

wherein Aib is α-Aminoisobutyric acid, and Deg is α, α Diethyl glycine effective to inhibit the proliferation of the tumor or cancer cells.

28. The method according to claim 27, wherein the tumor or cancer cells are adenocarcinoma of the colon, breast, lung, prostate, kidney or leukemia or lymphoma.

29. A method for inhibiting the proliferation of endothelial cells comprising contacting the endothelial cells in vitro with an amount of a peptide selected from the group consisting of:

Aib-Met-Tyr-Pro-Thr-Tyr-Aib-Lys-OH (SEQ ID NO: 8)

D-Leu-Met-Tyr-Pro-Thr-Tyr-Aib-Lys-OH (SEQ ID NO: 9)

Leu-Met-Tyr-Pro-Thr-D-Tyr-Leu-Lys-OH (SEQ ID NO: 10)

Leu-Met-Tyr-Pro-Thr-Tyr-D-Leu-Lys-OH (SEQ ID NO: 11)

Leu-Met-D-Tyr-Pro-Thr-Tyr-D-Leu-Lys-OH (SEQ ID NO: 12)

D-Leu-Met-Tyr-Pro-Thr-Tyr-D-Leu-Lys-OH (SEQ ID NO: 13)

Aib-Met-Tyr-Pro-Thr-Tyr-Deg-Lys-OH (SEQ ID NO: 14)

D-Leu-Met-Tyr-Pro-Thr-Tyr-Deg-Lys-OH (SEQ ID NO: 15)

D-Phe-Gln-Trp-Aib-Val-Gly-His-Leu-NH$_2$ (SEQ ID NO: 16)

D-Phe-Gln-Trp-Ala-Val-Aib-His-Leu-NH$_2$ (SEQ ID NO: 17)

D-Phe-Gln-Trp-Aib-Val-Gly-His-Ile-NH$_2$ (SEQ ID NO: 18)

D-Phe-Gln-Trp-Ala-Val-Aib-His-Ile-NH$_2$ (SEQ ID NO: 19)

Aib-Met-Gln-Trp-Phe-Aib-NH$_2$ (SEQ ID NO: 20)

D-Leu-Met-Gln-Trp-Phe-Aib-NH$_2$ (SEQ ID NO: 21)

D-Arg-Pro-Lys-Aib-Gln-D-Trp-Aib-Leu-NH$_2$ (SEQ ID NO: 22)

Ala-Aib-Cys-Lys-Asn-Phe-Phe-D-Trp-Lys-Thr-Phe-Thr-Ser-Cys (3-14 Disulphide Bond) (SEQ ID NO: 23).

Ala-Aib-Cys-Lys-Asn-Phe-Phe-D-Trp-Lys-Thr-Phe-Thr-Ser-Cys (SEQ ID NO: 24) and

D-Phe-Cys-Tyr-D-Trp-Lys-Thr-Aib-Thr-NH$_2$ (SEQ ID NO: 25)

wherein Aib is α-Aminoisobutyric acid, and Deg is α, α Diethyl glycine effective to inhibit the proliferation of the tumor or cancer cells.

30. A method of inhibiting the migration of tumor or cancer cells which comprises contacting the tumor or cancer cells in vitro with an amount of a peptide selected from the group consisting of:

Aib-Met-Tyr-Pro-Thr-Tyr-Aib-Lys-OH (SEQ ID NO: 8)

D-Leu-Met-Tyr-Pro-Thr-Tyr-Aib-Lys-OH (SEQ ID NO: 9)

Leu-Met-Tyr-Pro-Thr-D-Tyr-Leu-Lys-OH (SEQ ID NO: 10)

Leu-Met-Tyr-Pro-Thr-Tyr-D-Leu-Lys-OH (SEQ ID NO: 11)

Leu-Met-D-Tyr-Pro-Thr-Tyr-D-Leu-Lys-OH (SEQ ID NO: 12)

D-Leu-Met-Tyr-Pro-Thr-Tyr-D-Leu-Lys-OH (SEQ ID NO: 13)

Aib-Met-Tyr-Pro-Thr-Tyr-Deg-Lys-OH (SEQ ID NO: 14)

D-Leu-Met-Tyr-Pro-Thr-Tyr-Deg-Lys-OH (SEQ ID NO:15)

D-Phe-Gln-Trp-Aib-Val-Gly-His-Leu-NH$_2$ (SEQ ID NO: 16)

D-Phe-Gln-Trp-Ala-Val-Aib-His-Leu-NH$_2$ (SEQ ID NO: 17)

D-Phe-Gln-Trp-Aib-Val-Gly-His-Ile-NH$_2$ (SEQ ID NO: 18)

D-Phe-Gln-Trp-Ala-Val-Aib-His-Ile-NH$_2$ (SEQ ID N: 19)

Aib-Met-Gln-Trp-Phe-Aib-NH$_2$ (SEQ ID NO: 20)

D-Leu-Met-Gln-Trp-Phe-Aib-NH$_2$ (SEQ ID NO: 21)

D-Arg-Pro-Lys-Aib-Gln-D-Trp-Aib-Leu-NH$_2$ (SEQ ID NO: 22)

Ala-Aib-Cys-Lys-Asn-Phe-Phe-D-Trp-Lys-Thr-Phe-Thr-Ser-Cys (3-14 Disulphide Bond) (SEQ ID NO: 23)

Ala-Aib-Cys-Lys-Asn-Phe-Phe-D-Trp-Lys-Thr-Phe-Thr-Ser-Cys (SEQ ID NO: 24) and

D-Phe-Cys-Tyr-D-Trp-Lys-Thr-Aib-Thr-NH$_2$ (SEQ ID NO: 25)

wherein Aib is α-Aminoisobutyric acid, and Deg is α, α Diethyl glycine effective to inhibit the migration of the tumor or cancer cells.

31. The method according to claim 30, wherein the tumor or cancer cells are adenocarcinomas of the colon, breast, lung, prostate, kidney or leukemia or lymphoma.

32. A method for inhibiting the growth of tubes from tumor or cancer cells which comprises contacting the tumor or cancer cells in vitro with an amount of a peptide selected from the group consisting of:

Aib-Met-Tyr-Pro-Thr-Tyr-Aib-Lys-OH (SEQ ID NO: 8)

D-Leu-Met-Tyr-Pro-Thr-Tyr-Aib-Lys-OH (SEQ ID NO: 9)

Leu-Met-Tyr-Pro-Thr-D-Tyr-Leu-Lys-OH (SEQ ID NO: 10)

Leu-Met-Tyr-Pro-Thr-Tyr-D-Leu-Lys-OH (SEQ ID NO: 11)

Leu-Met-D-Tyr-Pro-Thr-Tyr-D-Leu-Lys-OH (SEQ ID NO: 12)

D-Leu-Met-Tyr-Pro-Thr-Tyr-D-Leu-Lys-OH (SEQ ID NO: 13)

Aib-Met-Tyr-Pro-Thr-Tyr-Deg-Lys-OH (SEQ ID NO: 14)

D-Leu-Met-Tyr-Pro-Thr-Tyr-Deg-Lys-OH (SEQ ID NO: 15)

D-Phe-Gln-Trp-Aib-Val-Gly-His-Leu-NH$_2$ (SEQ ID NO: 16)

D-Phe-Gln-Trp-Ala-Val-Aib-His-Leu-NH$_2$ (SEQ ID NO: 17)

D-Phe-Gln-Trp-Aib-Val-Gly-His-Ile-NH$_2$ (SEQ ID NO: 18)

D-Phe-Gln-Trp-Ala-Val-Aib-His-Ile-NH$_2$ (SEQ ID NO: 19)

Aib-Met-Gln-Trp-Phe-Aib-NH$_2$ (SEQ ID NO: 20)

D-Leu-Met-Gln-Trp-Phe-Aib-NH$_2$ (SEQ ID NO: 21)

D-Arg-Pro-Lys-Aib-Gln-D-Trp-Aib-Leu-NH$_2$ (SEQ ID NO: 22)

Ala-Aib-Cys-Lys-Asn-Phe-Phe-D-Trp-Lys-Thr-Phe-Thr-Ser-Cys (3-14 Disuilphide Bond) (SEQ ID NO: 23)

Ala-Aib-Cys-Lys-Asn-Phe-Phe-D-Trp-Lys-Thr-Phe-Thr-Ser-Cys (SEQ ID NO: 24) and

D-Phe-Cys-Tyr-D-Trp-Lys-Thr-Aib-Thr-NH$_2$ (SEQ ID NO: 25)

wherein Aib is α-Aminoisobutyric acid, and Deg is α, α Diethyl glycine effective to inhibit the migration of the tumor or cancer cells.

33. The method according to claim 32, wherein the tumor or cancer cells are adenocarcinomas of the colon, breast, lung, prostate, kidney or leukemia or lymphomas.

* * * * *